(12) United States Patent
Sirat et al.

(10) Patent No.: US 7,515,262 B2
(45) Date of Patent: Apr. 7, 2009

(54) CRYSTAL GRATING APPARATUS

(75) Inventors: Gabriel Sirat, Rehovot (IL); Daniel Neuhauser, Los Angeles, CA (US); Kalman Wilner, Ramat Gan (IL); David Vaknin, Jerusalem (IL)

(73) Assignee: Specrys Ltd., Rechovot (IL)

( * ) Notice: Subject to any disclaimer, the term of this patent is extended or adjusted under 35 U.S.C. 154(b) by 73 days.

(21) Appl. No.: 10/542,865

(22) PCT Filed: Jan. 21, 2004

(86) PCT No.: PCT/IL2004/000057

§ 371 (c)(1),
(2), (4) Date: Jan. 10, 2006

(87) PCT Pub. No.: WO2004/064969

PCT Pub. Date: Aug. 5, 2004

(65) Prior Publication Data

US 2006/0126067 A1    Jun. 15, 2006

Related U.S. Application Data

(60) Provisional application No. 60/441,298, filed on Jan. 22, 2003.

(51) Int. Cl.
*G01J 3/02* (2006.01)
*G01J 3/30* (2006.01)

(52) U.S. Cl. .................. 356/326; 356/327; 356/328

(58) Field of Classification Search .......... 385/13; 356/310, 326, 327, 328, 330
See application file for complete search history.

(56) References Cited

U.S. PATENT DOCUMENTS

| 4,448,529 | A  | * | 5/1984  | Krause ............... 356/310 |
| 5,570,180 | A  | * | 10/1996 | Nagai ................ 356/330 |
| 6,002,479 | A  |   | 12/1999 | Barwicz et al. |
| 6,031,609 | A  | * | 2/2000  | Funk et al. .......... 356/310 |
| 6,782,205 | B2 | * | 8/2004  | Trisnadi et al. ....... 398/94 |
| 7,110,675 | B2 | * | 9/2006  | Carey ................. 398/90 |

OTHER PUBLICATIONS

Ben-Yosef et al. "Real-Time Spatial Filtering Utilizing the Piezoelectric-Elasto-Optic Effect", Journal of Modern optics, 29 (4): 419-423, 1982. Abstract.

* cited by examiner

*Primary Examiner*—F. L Evans

(57) ABSTRACT

Apparatus for analyzing light having at least one wavelength, the apparatus comprising: (a) a light deflector for deflecting the light so as to provide a deflected light beam characterized by at least one wavelength-dependent angle, respectively corresponding to the at least one wavelength of the light; (b) an encoder, capable of encoding the deflected light beam so as to provide an encoded light beam characterized by at least one angle-dependent polarization state, respectively corresponding to the at least one wavelength-dependent angle; and (c) a decoder, for decoding the encoded light beam so as to determine at least one spectral component of the light.

46 Claims, 6 Drawing Sheets

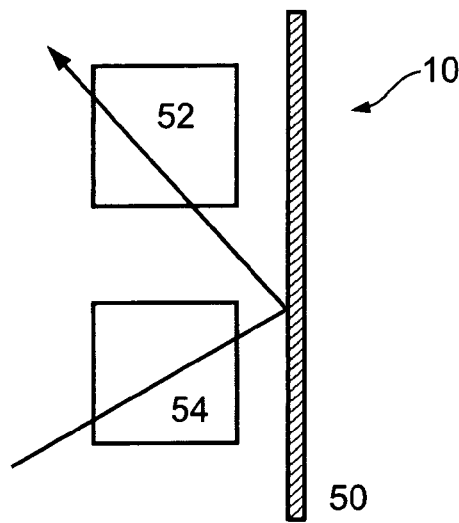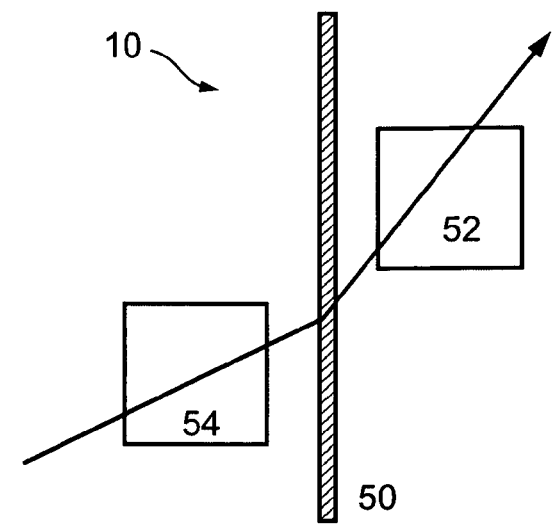
Fig. 6a    Fig. 6b
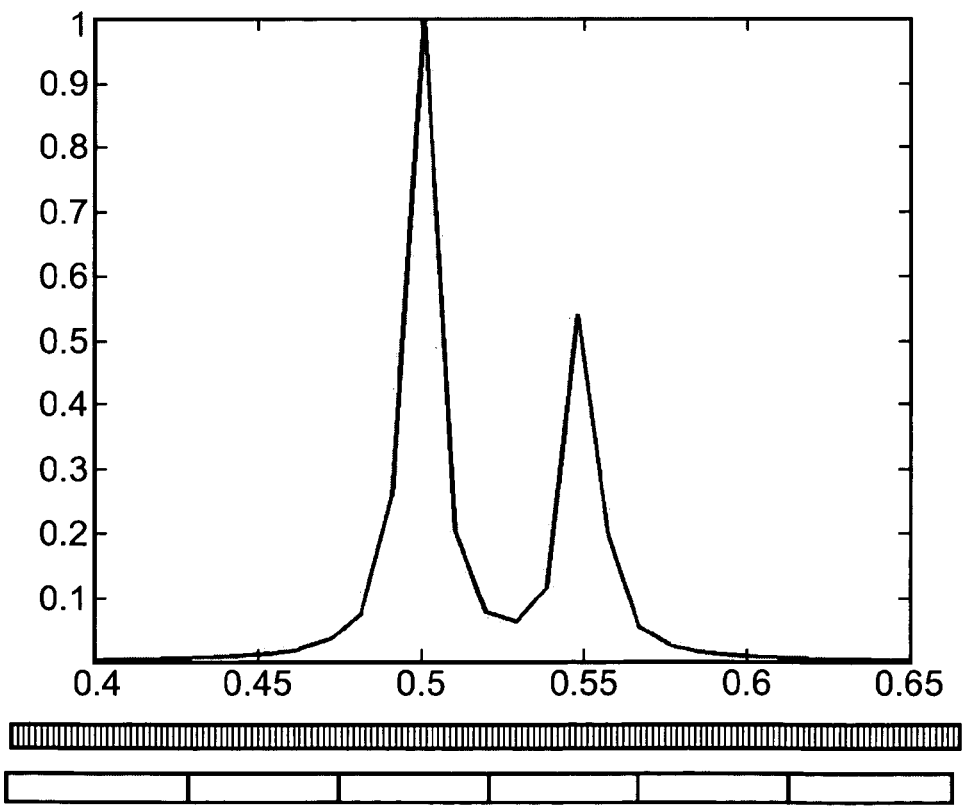
Fig. 7

CRYSTAL GRATING APPARATUS

RELATED PATENT APPLICATION

This application is a National Phase Application of PCT/IL2004/000057 having International Filing Date of 21 Jan. 2004, which claims the benefit of U.S. Provisional Patent Application No. 60/441,298 filed 22 Jan. 2003. The contents of the above Application are all incorporated herein by reference.

FIELD AND BACKGROUND OF THE INVENTION

The present invention relates to measurement, filtration or separation of light, and, more particularly, to wavelength measurement or separation of light according to its spectral components.

Compact and cost-effective wavelength meters are in great demand for numerous applications, including instrumentation and wavelength division multiplexed (WDM) communications systems.

An optical wavelength meter is an electronic instrument that measures the wavelength of a light signal input thereto. An optical multi-wavelength meter is one that can simultaneously measure the wavelengths of multiple signals of light such as channels in a WDM system.

A spectrometer is a device which receives a light signal as an input and produces as an output a light signal which is spread out, or dispersed, in space according to the different spectral components, or colors, of the input light signal. A detector attached to the spectrometer can analyze the output signal in order to quantify the amount of each wavelength component present in the input signal. High resolution spectrometers are used in a wide variety of optical applications such as the above motioned WDM systems. High resolution spectrometers are also used as polarization mode dispersion (PMD) sensors, or as measuring devices to obtain the optical power spectrum of any optical field propagating through an optical network.

In life science, wavelength meters and spectrometers are often used as components in optical sensors for the purpose of measuring or monitoring analytes in a sample or in vivo. For example, a fluid sample of unknown analyte content is tested by inserting the sample into a sample chamber where it contacts an analytical element. Using an optical sensor, changes in the optical properties of the analytical element are recorded and used for determining the characteristics of the analyte of interest in the unknown.

In the field of imaging, measuring the spectral content of the illumination source is necessary for the purpose of processing the image to achieve a better resolution or realistic colors. In black and white imaging, for example, the measurement can be performed with a "light meter." The meter is pointed at the light source, which would be straight up for daylight or towards a spotlight if it were focused on the object of interest. In color imaging and photography, a more sophisticated measurement is to be used. Rather than measuring a single quantity, a wavelength meter or a spectrometer has to measure numerous points across the visual light spectrum and make a graph of the power at each wavelength that it has found. Once this graph is known, then an accurate representation of the original image can be constructed by removing the influence of the light source from the original scene.

Spectrometers and wavelength meters are also used in the field of colorimetry where a precise determination of color content of a sample material is vital to the successful outcome of a project. For example, in the automotive industry, exact color matching is essential when a portion of a vehicle is being painted so that the repainted portion matches the original color of the rest of the vehicle. It is recognized that the ability to repaint only the repaired portion of the vehicle rather than repainting the entire vehicle leads to considerable savings of money, materials and time. In the aerospace industry, one is often interested in an optimum color scheme for an aircraft which minimizes its ability to be detected by the enemy. It is therefore vital that the exact color specified can be provided by the paint supplier.

In general, spectrometers are classified as either scanning or non-scanning spectrometers. While scanning spectrometers can exhibit very high spectral resolutions, the fact that they must be scanned limits their usefulness to the domain of optical signals whose spectrum does not change appreciably over the required scan time. Non-scanning spectrometers provide an attractive method for estimating the power spectral density of an incident optical signal because the far-field pattern, which serves as the spectral estimate, is available more or less instantaneously and therefore can be used to estimate the power spectrum of very short-lived signals.

Spectrometers and wavelength meters often utilize diffraction gratings to diffract incident light and form a far-field optical pattern from which a power spectral estimate may be obtained. Diffraction gratings typically include a plurality of periodically and equally spaced grooves that act as scattering sites to scatter the incident light. The light scattered from each of the grooves creates an interference pattern a distance away from the grating, known as the far-field diffraction or Fraunhofer pattern. The resulting far-field pattern exhibits regions or peaks of high intensity for a given wavelength, which are commonly called diffraction orders.

A typical spectrometer consists of a slit, a collimator lens, a dispersive optic (e.g., diffraction grating), an objective lens or lenses for focusing the various wavelengths and a photometer for measuring the intensity of the various wavelengths. A light source is typically sampled by an optical fiber so that a portion of the light is directed to a slit which expands the light to a beam. The beam is collimated by a lens and impinges on the diffraction grating from which the beam is dispersed at several angles depending on the wavelengths of the light. The wavelengths of interest are then refocused by an objective lens and measured by a photometer.

Wavelength or wavelengths of light may be measured using a device called Michelson interferometer, which measures an interference signal between two light beams generated from the optical signal being measured. More specifically, in such devices a wavefront of light is separated into two beams so as to introduce of an optical path difference between such beams. This causes modulation of light intensity due to interference between the two beams, such that each optical wavelength present in the input light generates its own modulation frequency. Thus, the spectral content of the input light can be decoded by using Fourier transform.

The optical path difference may be introduced, for example, by allowing one light beam to traverse a fixed path, while varying the path of another light beam using a mirror, so that the interference signal is a function of the mirror position. In another method, optical path difference is introduced between two rays with orthogonal polarization directions inside the double-refractive crystal. The waves corresponding to ordinary and extraordinary polarizations separate upon incidence on the crystal and travel with different velocities. After passing through the crystal, the rays exhibit a phase delay between them, which is proportional to crystal thickness. The two rays then interfere with each other after passing through a polarizing analyzer. The resulting intensity variations, which bear the signature of presented spectral components, are transformed or converted into an electrical signal by a photodetector. The electrical signal is thereby recorded for analysis.

Prior art spectrometers and wavelength meters suffer from limited resolution which is inherently imposed by the grating parameter or the refractive crystal characteristics. In addition prior art spectrometers and wavelength meters have rather poor performances in cases where the beam of light is not fully collimated prior to the measurement.

There is thus a widely recognized need for, and it would be highly advantageous to have, a method and apparatus for wavelength measurement or separation of light according to its spectral components devoid of the above limitations.

SUMMARY OF THE INVENTION

According to one aspect of the present invention there is provided an apparatus for analyzing light having at least one wavelength, the apparatus comprising: (a) a light deflector for deflecting the light so as to provide a deflected light beam characterized by at least one wavelength-dependent angle, respectively, corresponding to the at least one wavelength of the light; (b) an encoder, capable of encoding the deflected light beam so as to provide an encoded light beam characterized by at least one angle-dependent polarization state, respectively, corresponding to the at least one wavelength-dependent angle; and (c) a decoder, for decoding the encoded light beam so as to determine at least one spectral component of the light.

According to still another aspect of the present invention there is provided an apparatus for analyzing light having at least one wavelength, the apparatus comprising, an encoder, a light deflector and a decoder; the encoder and the light deflector being designed and constructed such that the light is encoded by the encoder to a first set of polarization states, deflected by the deflector to a set of wavelength-dependent angles, reflected back to the encoder, encoded by the encoder to a second set of polarization states and impinges on the decoder; the decoder being operable to decode the second set of polarization states so as to determine at least one spectral component of the light.

According to another aspect of the present invention there is provided an apparatus for measuring a wavelength of a monochromatic light, the apparatus comprising: (a) a light deflector for deflecting the monochromatic light at a wavelength-dependent angle; (b) an encoder, capable of encoding the monochromatic light according to the wavelength-dependent angle thereby to provide an encoded light beam; and (c) a decoder, for decoding the encoded light beam so as to determine the wavelength of a monochromatic light.

According to yet another aspect of the present invention there is provided a Bragg sensor system for detecting vibrations, the system having an apparatus for analyzing light having at least one wavelength, the apparatus comprising: (a) a light deflector for deflecting the light so as to provide a deflected light beam characterized by a plurality of wavelength-dependent angles, respectively, corresponding to the plurality of wavelengths of the optical signal; (b) an encoder, capable of encoding the deflected light beam so as to provide an encoded light beam characterized by a plurality of angle-dependent polarization states, respectively, corresponding to the plurality of wavelength-dependent angles; and (c) a decoder, for decoding the encoded light beam so as to determine the plurality of wavelengths of the optical signal, thereby to detect vibrations of the light deflector and/or the encoder.

According to still an additional another aspect of the present invention there is provided a communications system having a multiplexing apparatus for generating an optical signal characterized by a plurality of wavelengths and a de-multiplexing apparatus, for extracting the information from the optical signal, the de-multiplexing apparatus comprising: (a) a light deflector for deflecting the light so as to provide a deflected light beam characterized by a plurality of wavelength-dependent angles, respectively, corresponding to the plurality of wavelengths of the optical signal; (b) an encoder, capable of encoding the deflected light beam so as to provide an encoded light beam characterized by a plurality of angle-dependent polarization states, respectively, corresponding to the plurality of wavelength-dependent angles; and (c) a decoder, for decoding the encoded light beam so as to determine the plurality of wavelengths of the optical signal.

According to further features in preferred embodiments of the invention described below, the apparati and/or systems further comprise a mechanism for varying at least one parameter representing at least one of the light deflector and the encoder so as to span a discrete basis of signals, each corresponding to one value of the at least one parameter.

According to still further features in the described preferred embodiments the decoder is operable to use the discrete basis of signals for determining the wavelength of a monochromatic light.

According to still further features in the described preferred embodiments the apparati and/or systems further comprise a beam splitter, for splitting the monochromatic light into two beams, each having a predetermined polarization According to still further features in the described preferred embodiments the apparati and/or systems further comprise at least one polarization rotator, designed and configured so as to rotate a polarization of the deflected light beam and/or a polarization of the encoded light beam.

According to still further features in the described preferred embodiments the apparati and/or systems further comprise a collimator for collimating the monochromatic light, prior to an impingement of the monochromatic light on the light deflector.

According to still further features in the described preferred embodiments the decoder is capable of generating a representative time-delay for each of the angle-dependent polarization state, and using the representative time-delay for determining the wavelength of the monochromatic light.

According to still further features in the described preferred embodiments the decoder is capable of generating a representative time-delay for each polarization state of the second set of polarization states, and using the representative time-delay for determining the at least one spectral component of the light.

According to still further features in the described preferred embodiments the apparati and/or systems further comprise a low-resolution optical device, for determining a low-resolution spectral range of the monochromatic light.

According to still further features in the described preferred embodiments the encoder is operable to generate at least one angle-dependent polarization phase-shift, thereby to provide the first and the second sets of polarization states.

According to still further features in the described preferred embodiments the encoder comprises at least one geometrical crystal filter characterized by at least one angle-dependent index of refraction.

According to still further features in the described preferred embodiments the apparati and/or systems further comprise at least one additional geometrical crystal filter, for polarizing the light prior to impinging of the monochromatic light on the light deflector.

According to still further features in the described preferred embodiments the apparati and/or systems further comprise a first mechanism for varying the angle-dependent polarization phase-shift.

According to still further features in the described preferred embodiments the first mechanism is operable to rotate the at least one geometrical crystal filter about an axis, so as to vary the angle-dependent polarization phase-shift.

According to still further features in the described preferred embodiments the apparati and/or systems further comprise a first polarization rotator, for rotating a polarization of the deflected light beam from a first polarization orientation to a second polarization orientation.

According to still further features in the described preferred embodiments the first polarization rotator is designed and constructed such that the second polarization orientation substantially equals an orientation of the at least one geometrical crystal filter.

According to still further features in the described preferred embodiments the apparati and/or systems further comprise a second polarization rotator, for rotating a polarization of the encoded light beam from the second polarization orientation to the first polarization orientation.

According to still further features in the described preferred embodiments the first mechanism is operable to generate a further deflection of the deflected light beam, the further deflection being time-dependent so that the angle-dependent polarization phase-shift varies.

According to still further features in the described preferred embodiments the first mechanism is a mirror.

According to still further features in the described preferred embodiments the first mechanism is operable to vary an effective length of the at least one geometrical crystal filter, thereby to vary the angle-dependent polarization phase-shift.

According to still further features in the described preferred embodiments the first mechanism is capable of applying a voltage on the at least one geometrical crystal filter, thereby to vary the effective length.

According to still further features in the described preferred embodiments a shape of the at least one geometrical crystal filter is selected such that when the first mechanism applies a translational motion thereto, the effective length is varied.

According to still further features in the described preferred embodiments the light deflector is a dynamic grating characterized by a grating equation and further wherein the first mechanism is operable to vary the grating equation, thereby to vary the wavelength-dependent angle, thereby also to vary the angle-dependent polarization phase-shift.

According to still further features in the described preferred embodiments the apparati and/or systems further comprise a collimator for collimating the light, prior to an impingement of the light on the light deflector.

According to still further features in the described preferred embodiments the decoder comprises: (i) a temporal polarization phase-shifter, communicating with an external clock, and capable of accumulating a time-dependent polarization phase-shift to the encoded light beam; and (ii) a polarization phase-shift analyzer, capable of analyzing the time-dependent polarization phase-shift so as to provide an optical signal having a time-dependent intensity, corresponding to the time-dependent polarization phase-shift.

According to still further features in the described preferred embodiments the decoder comprises: (i) a temporal polarization phase-shifter, communicating with an external clock, and capable of accumulating a time-dependent polarization phase-shift to each polarization state of the second set of polarization states; and (ii) a polarization phase-shift analyzer, capable of analyzing the time-dependent polarization phase-shift so as to provide an optical signal having a time-dependent intensity, corresponding to the time-dependent polarization phase-shift.

According to an additional aspect of the present invention there is provided a method of analyzing light having at least one wavelength, the method comprising: (a) deflecting the light so as to provide a deflected light beam characterized by at least one wavelength-dependent angle, respectively, corresponding to the at least one wavelength of the light; (b) encoding the deflected light beam so as to provide an encoded light beam characterized by at least one angle-dependent polarization state, respectively, corresponding to the at least one wavelength-dependent angle; and (c) decoding the encoded light beam so as to determine at least one spectral component of the light.

According to yet an additional aspect of the present invention there is provided a method of measuring a wavelength of a monochromatic light, the method comprising: (a) deflecting the monochromatic light at a wavelength-dependent angle; (b) encoding the monochromatic light according to the wavelength-dependent angle thereby providing an encoded light beam; and (c) decoding the encoded light beam so as to determine the wavelength of the monochromatic light.

According to further features in preferred embodiments of the invention described below, the method further comprises polarizing, at least once, the light prior to step (a).

According to still further features in the described preferred embodiments the method further comprises: (d) varying at least one parameter representing at least one of steps (a) and (b) and repeating steps (a)-(b) at least once so as to span a discrete basis of signals, each corresponding to one value of the at least one parameter; and (e) using the discrete basis of signals for determining the at least one spectral component of the light.

According to still further features in the described preferred embodiments the method further comprises splitting the light into two beams, each having a predetermined polarization.

According to still further features in the described preferred embodiments the method further comprises rotating a polarization of the deflected light beam and/or a polarization of the encoded light beam.

According to still further features in the described preferred embodiments the splitting the light is by a double refraction plate.

According to still further features in the described preferred embodiments the method further comprises varying the angle-dependent polarization phase-shift varies with time.

According to still further features in the described preferred embodiments the method further comprises varying the angle-dependent polarization phase-shift.

According to still further features in the described preferred embodiments the varying the angle-dependent polarization phase-shift is by rotating the at least one geometrical crystal filter.

According to still further features in the described preferred embodiments the method further comprises rotating a polarization of the deflected light beam from a first polarization orientation to a second polarization orientation.

According to still further features in the described preferred embodiments the the rotating the polarization of the deflected light is such that the second polarization orientation substantially equals an orientation of the at least one geometrical crystal filter.

According to still further features in the described preferred embodiments the method further comprises rotating a polarization of the encoded light beam from the second polarization orientation to the first polarization orientation.

According to still further features in the described preferred embodiments the varying the angle-dependent polarization phase-shift is by generating a further deflection of the deflected light beam, the further deflection being time-dependent.

According to still further features in the described preferred embodiments the generating the further deflection is by a mirror.

According to still further features in the described preferred embodiments the varying the angle-dependent polarization phase-shift is by varying an effective length of the at least one geometrical crystal filter.

According to still further features in the described preferred embodiments the varying the effective length is by applying a voltage on the at least one geometrical crystal filter.

According to still further features in the described preferred embodiments a shape of the at least one geometrical crystal filter is selected such that when a translational motion is applied thereto, the effective length is varied.

According to still further features in the described preferred embodiments the varying the effective length is by applying the translational motion to the at least one geometrical crystal filter.

According to still further features in the described preferred embodiments the deflecting is by a dynamic grating characterized by a grating equation and further wherein the varying the angle-dependent polarization phase-shift is by varying the grating equation, thereby varying the wavelength-dependent angle, thereby also varying the angle-dependent polarization phase-shift.

According to still further features in the described preferred embodiments the decoding the encoded light beam is by obtaining a plurality of parameters, each corresponding to one angle dependent polarization phase-shift, and analyzing the plurality of parameters thereby decoding the encoded light beam.

According to still further features in the described preferred embodiments the analyzing the plurality of parameters is by linear decomposition.

According to still further features in the described preferred embodiments the analyzing the plurality of parameters is by linear prediction.

According to still further features in the described preferred embodiments the analyzing the plurality of parameters is by a maximum entropy method.

According to still further features in the described preferred embodiments the analyzing the plurality of parameters is by harmonic inversion.

According to still further features in the described preferred embodiments the method further comprises collimating the light, prior to an impingement of the light on the light deflector.

According to still further features in the described preferred embodiments the method further comprises polarizing the light prior to impinging of the light on the light deflector.

According to still further features in the described preferred embodiments the method further comprises generating a representative time-delay for each of the angle-dependent polarization state, and using the representative time-delay for determining the at least one spectral component of the light.

According to still further features in the described preferred embodiments the method further comprises filtering a portion of the light, prior to the step of deflecting, the step of encoding and/or the step of decoding.

According to still further features in the described preferred embodiments the method further comprises determining a low-resolution spectral range of the light.

According to still further features in the described preferred embodiments the determining the low-resolution spectral range of the light is by an additional geometrical crystal filter having a free spectral range which is different than a free spectral range of the at least one geometrical crystal filter.

According to still further features in the described preferred embodiments the method further comprises polarizing the light at least once, prior to step (a).

According to still further features in the described preferred embodiments the step (b) is repeated at least once.

According to still further features in the described preferred embodiments the step (e) is done by a mathematical transform.

According to still further features in the described preferred embodiments the deflecting is by a grating.

According to still further features in the described preferred embodiments the deflecting is by a prism.

According to still further features in the described preferred embodiments the encoding comprises generating at least one angle-dependent polarization phase-shift, thereby providing the angle-dependent polarization state.

According to still further features in the described preferred embodiments the generating the at least one angle-dependent polarization phase-shift is done so as to generate a zero or small polarization phase-shift for a predetermined set of wavelengths and a non-zero polarization phase-shift for wavelengths other than the predetermined set of wavelengths.

According to still further features in the described preferred embodiments the generation of the at least one angle-dependent polarization phase-shift is by at least one geometrical crystal filter characterized by at least one angle-dependent index of refraction.

According to still further features in the described preferred embodiments the method further comprises splitting the encoded light beam into two secondary polarized light beams, and calculating a contrast function between the two secondary polarized light beams.

According to still further features in the described preferred embodiments the decoding the encoded light beam is by a mathematical transform.

According to still further features in the described preferred embodiments the mathematical transform is elected from the group consisting of a Fourier transform, a Gabor transform, a Haar transform, a Hartley transform, a sine transform, a cosine transform, a Hadamard transform and a wavelet transform.

According to still further features in the described preferred embodiments the decoding the encoded light beam is by a calibration table.

According to still further features in the described preferred embodiments the decoding the encoded light beam is by least square fitting.

According to still further features in the described preferred embodiments the decoding the encoded light beam is by a compensated pseudo-phase method.

According to still further features in the described preferred embodiments the decoding comprises: (i) accumulating a time-dependent polarization phase-shift to the encoded light beam; and (ii) analyzing the time-dependent polarization phase-shift so as to provide an optical signal having a time-dependent intensity, corresponding to the time-dependent polarization phase-shift.

According to still further features in the described preferred embodiments the accumulating the time-dependent polarization phase-shift is by an optical element selected from the group consisting of a liquid crystal light valve and a piezoelectric crystal.

According to still further features in the described preferred embodiments the method further comprises converting the optical signal to electrical signal.

According to still further features in the described preferred embodiments the converting the optical signal to electrical signal is by an optical converter selected from the group consisting of a charge coupled device, a CMOS detector, a photovoltaic detector, a pin detector, a photodiode, a charge injection device, an image intensifier, a photoconductor detector, an avalanche detector, a photomultiplier and any combination thereof.

According to still further features in the described preferred embodiments the method further comprises filtering a portion of the light, prior the step of deflecting, the step of encoding and/or the step of decoding.

According to still further features in the described preferred embodiments the method further comprises reducing a spot size of the light prior to the step of deflecting.

According to still further features in the described preferred embodiments the method further comprises increasing angular dispersion of the deflected light beam, prior to the step of decoding, thereby optimizing a wavelength resolution.

According to still further features in the described preferred embodiments the determination of the low-resolution spectral range is by directly using the at least one wavelength-dependent angle.

According to still further features in the described preferred embodiments the directly using the at least one wavelength-dependent angle is by a position sensing device, whereby a position of the deflected light beam corresponds to a respective wavelength-dependent angle.

According to still further features in the described preferred embodiments the position sensing device is selected from the group consisting of a charge coupled device, a CMOS detector, a photovoltaic detector, a pin detector, a photodiode, a charge injection device, an image intensifier, a photoconductor detector, an avalanche detector and a photomultiplier.

According to still further features in the described preferred embodiments the method further comprises sensing changes in environmental conditions, influencing the deflected light beam and/or the encoded light beam.

According to still further features in the described preferred embodiments the analysis of the light is characterized by a sub picometer resolution.

According to still further features in the described preferred embodiments the analysis of the light is characterized by a sub nanometer resolution.

According to still further features in the described preferred embodiments a total analysis time of the light is from about 1 nanosecond to a few hours.

According to still further features in the described preferred embodiments the analysis of the light is characterized by a detectivity of from about −80 db to about −0 db.

According to still further features in the described preferred embodiments the beam splitter comprises a double refraction plate.

According to still further features in the described preferred embodiments the light deflector is selected from the group consisting of a grating and a prism.

According to still further features in the described preferred embodiments the grating is characterized by a first grating equation in a first dimension and a second grating equation in a second dimension.

According to still further features in the described preferred embodiments the wavelength-dependent angle is characterized by a predetermined dispersion equation.

According to still further features in the described preferred embodiments the encoder is calibrated so as to generate a zero or small polarization phase-shift for a predetermined set of wavelengths and a non-zero polarization phase-shift for wavelengths other than the predetermined set of wavelengths.

According to still further features in the described preferred embodiments the predetermined set of wavelengths comprises a central wavelength and a repetitive set of wavelengths being associated with the central wavelength.

According to still further features in the described preferred embodiments the polarization phase-shift is selected so as to minimize diffraction effects.

According to still further features in the described preferred embodiments the angle-dependent polarization phase-shift varies with time.

According to still further features in the described preferred embodiments the encoder comprises at least one geometrical crystal filter characterized by at least one angle-dependent index of refraction.

According to still further features in the described preferred embodiments the at least one geometrical crystal filter is selected from the group consisting of a birefringent crystal and quartz.

According to still further features in the described preferred embodiments the birefringent crystal is calcite.

According to still further features in the described preferred embodiments the at least one geometrical crystal filter is selected from the group consisting of at least one on-axis crystal, at least one off-axis crystal and a combination of at least one on-axis crystal and at least one off-axis crystal.

According to still further features in the described preferred embodiments the decoder is capable of splitting the encoded light beam into two secondary polarized light beams, and calculating a contrast function between the two secondary polarized light beams.

According to still further features in the described preferred embodiments the decoder is capable of generating a representative time-delay for each of the angle-dependent polarization state, and using the representative time-delay for determining the at least one spectral component of the light.

According to still further features in the described preferred embodiments the temporal polarization phase-shifter is selected from the group consisting of a liquid crystal light valve and a piezoelectric crystal.

According to still further features in the described preferred embodiments the piezoelectric crystal is a single resonance piezoelectric crystal.

According to still further features in the described preferred embodiments the piezoelectric crystal is a multi resonance piezoelectric crystal.

According to still further features in the described preferred embodiments the piezoelectric crystal Is selected from the group consisting of a cubic piezoelectric crystal, a triagonal piezoelectric crystal and a hexagonal crystal.

According to still further features in the described preferred embodiments the piezoelectric crystal is selected from the group consisting of quartz, lithium niobate and lithium tantalate.

According to still further features in the described preferred embodiments the decoder further comprises an optical converter, for converting the optical signal to electrical signal.

According to still further features in the described preferred embodiments the optical converter is selected from the group consisting of a charge coupled device, a CMOS detector, a photovoltaic detector, a pin detector, a photodiode, a charge injection device, an image intensifier, a photoconductor detector, an avalanche detector, a photomultiplier and any combination thereof.

According to still further features in the described preferred embodiments the apparati and/or systems further comprise at least one filter for filtering a portion of the light, prior to an impingement on the deflector, the encoder and/or the decoder.

According to still further features in the described preferred embodiments the apparati and/or systems further comprise a first anamorphic prism, positioned so as to reduce a spot size of the light prior to impingement of the light on the deflector.

According to still further features in the described preferred embodiments the apparati and/or systems further comprise a second anamorphic prism, positioned so as to increase angular dispersion of the deflected light beam, prior to impingement of the deflected light beam on the decoder, thereby to optimize a wavelength resolution.

According to still further features in the described preferred embodiments the low-resolution optical device comprises an additional geometrical crystal filter, and further wherein a free spectral range of the additional geometrical crystal filter is different than a free spectral range of the at least one geometrical crystal filter.

According to still further features in the described preferred embodiments the free spectral range of the additional geometrical crystal filter is substantially larger than the free spectral range of the at least one geometrical crystal filter.

According to still further features in the described preferred embodiments the low-resolution optical device is capable of directly using the at least one wavelength-dependent angle so as to determine the low-resolution spectral range.

According to still further features in the described preferred embodiments the low-resolution optical device is a position sensing device, whereby a position of the deflected light beam corresponds to a respective wavelength-dependent angle.

According to still further features in the described preferred embodiments the low-resolution optical device is selected from the group consisting of a charge coupled device, a CMOS detector, a photovoltaic detector, a pin detector, a photodiode, a charge injection device, an image intensifier, a photoconductor detector, an avalanche detector and a photomultiplier.

According to still further features in the described preferred embodiments the apparatus is characterized by a sub picometer resolution.

According to still further features in the described preferred embodiments the apparatus is characterized by a sub nanometer resolution.

According to still further features in the described preferred embodiments the apparatus is characterized by a total analysis time of from about 1 nanosecond to a few hours.

According to still further features in the described preferred embodiments the apparatus is characterized by a detectivity of from about −80 db to about −0 db.

According to still further features in the described preferred embodiments the apparati or systems serve as a component in a wavelength amplifying system.

According to still further features in the described preferred embodiments the apparati or systems serve as a component in an optical sensor.

According to still further features in the described preferred embodiments the apparati or systems serve as a component in a spectrograph.

According to still further features in the described preferred embodiments the apparati or systems serve as a component in an imaging spectrograph.

According to still further features in the described preferred embodiments the apparati or systems serve as a component in a time frequency spectrograph.

According to still further features in the described preferred embodiments the apparati or systems serve as a component in a telecentric imaging system.

According to still further features in the described preferred embodiments the apparati or systems serve as a component in an optical storage medium.

According to still further features i the described preferred embodiments the apparati or systems serve as a component in an optical communication system.

According to still further features in the described preferred embodiments the apparati or systems serve as a component in a tunable laser system.

According to still further features in the described preferred embodiments the apparati or systems serve as a component in a lithography system.

According to still further features in the described preferred embodiments the apparati or systems serve as a component in an optical computing system.

According to still further features in the described preferred embodiments the apparati or systems serve as a component in a fiber Bragg sensor.

According to still further features in the described preferred embodiments the apparati or systems serve for stabilizing laser radiation.

According to still further features in the described preferred embodiments the apparati or systems serve for monitoring optical pulses.

According to still further features in the described preferred embodiments the apparati or systems serve for modulating a light source.

According to still further features in the described preferred embodiments the apparati or systems serve for discriminating between Raman emission and fluorescence.

According to still further features in the described preferred embodiments the apparati or systems serve for discriminating between different light sources.

According to still further features in the described preferred embodiments the apparati or systems serve for testing a multi-lasers test system.

According to still further features in the described preferred embodiments the apparati or systems serve for generating frequency multiplexed signals.

According to still further features in the described preferred embodiments the apparati or systems serve for sensing changes in environmental conditions, influencing the deflected light beam and/or the encoded light beam.

According to still further features in the described preferred embodiments the changes in the environmental conditions are selected from the group consisting of vibrations, changes in temperature, changes in pressure, changes in magnetic field and changes in electric field.

The present invention successfully addresses the shortcomings of the presently known configurations by providing an apparatus and method for measuring a wavelength, or analyzing light according to its wavelength.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessarily for a fundamental understanding of the invention, the description taken with the drawings making apparent to those skilled in the art how the several forms of the invention may be embodied in practice.

In the drawings:

FIGS. 6a-b are schematic illustrations of the apparatus of FIGS. 1a-c in the embodiment in which the light preferably passes an encoder two times;

FIG. 7 shows a spectrum, decoded by a multi-wavelength meter, in which each peak is covered by a separate detector, according to a preferred embodiment of the present invention;

DESCRIPTION OF THE PREFERRED EMBODIMENTS

Figure 1A:
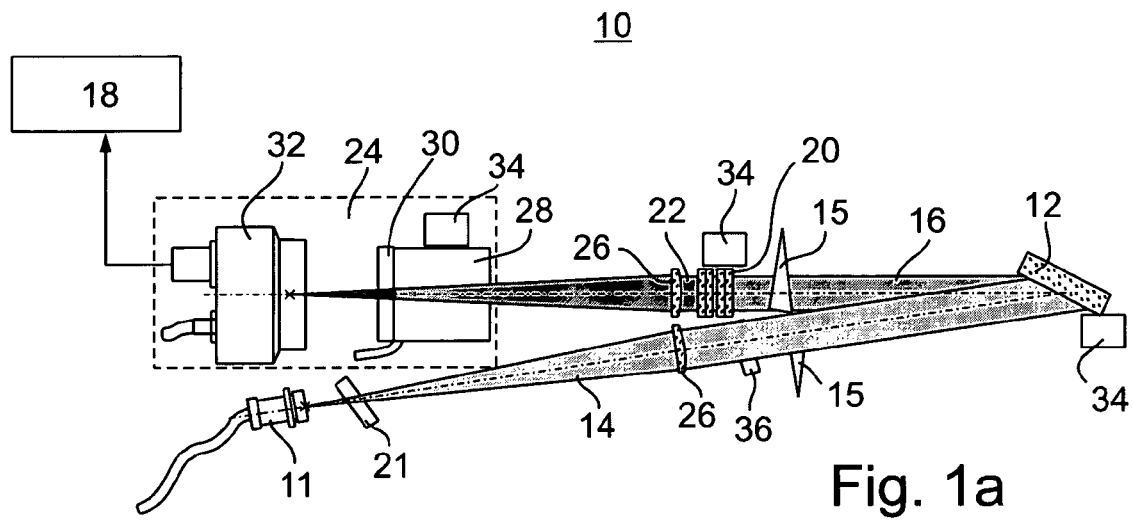
FIGS. 1a-c are schematic illustrations of an apparatus for analyzing light, according to a preferred embodiment of the present invention.

The present invention is of a method and apparatus form measuring, filtering or separating light to its spectral components. Specifically, the present invention can be used to determine the wavelength of a monochromatic light or the spectral components of a multi-chromatic light in many optical-related applications, such as, but not limited to, spectrographs, imaging spectrographs, time-frequency spectrographs, wavelength amplifying systems, telecentric imaging systems, optical storage media, optical communication systems, tunable laser systems, lithography systems, optical computing systems and a variety of sensors.

The principles and operation of a method and apparatus for analyzing light according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
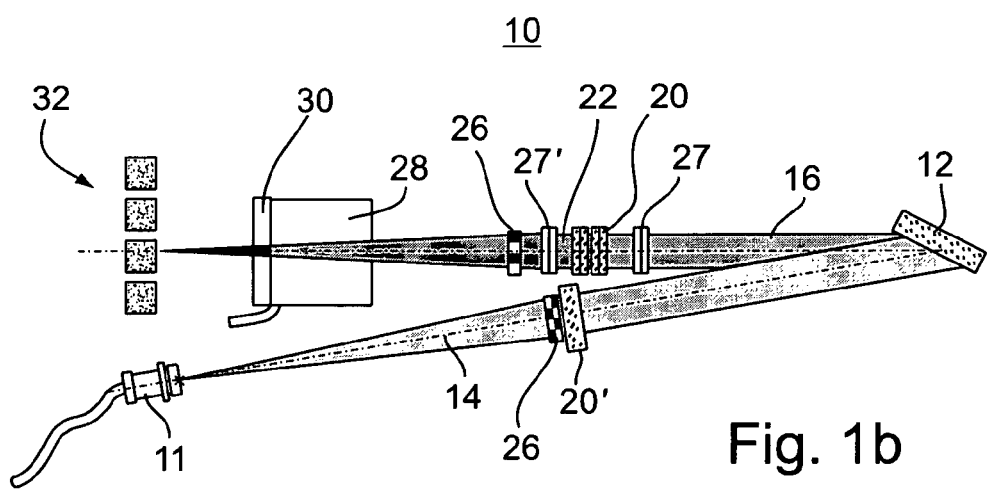
Figure 1C:
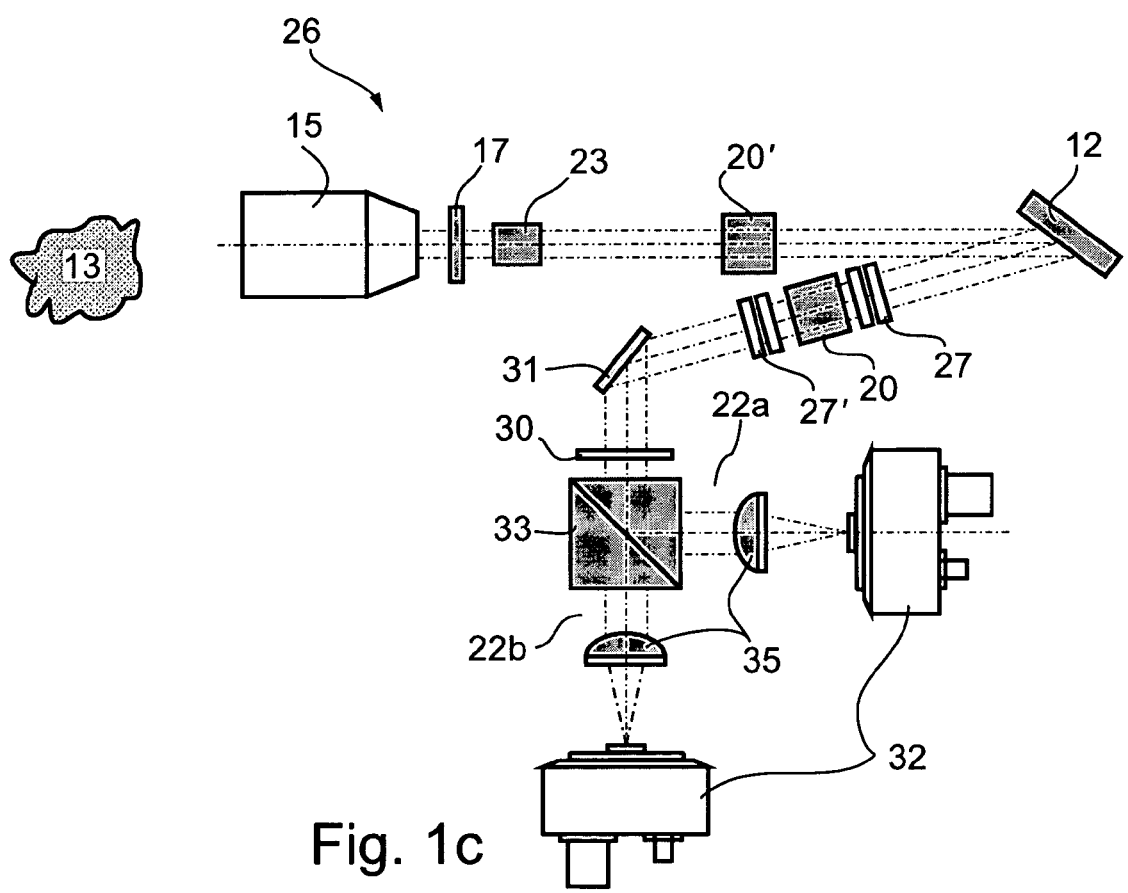

Referring now to the drawings, FIGS. 1a-c illustrate an apparatus 10 for analyzing light 14. As further detailed in the Examples section that follows, apparatus 10 can be employed in many applications, as a wavelength meter, a multi-wavelength meter or a spectrometer. Following is a general description of the principles and operations of apparatus 10, according to a preferred embodiment of the present invention.

Hence, light 14 may be emitted, for example, from an optical fiber 11 (FIGS. 1a-b) or any other light source 13 (FIG. 1c), such as, but not limited to, a lamp, a laser device and any type of fluorescent material. Additionally, light 14 can be a result of an optical reflection, from an illuminated scene, or transmission, e.g., through a light transmissive substrate, which may be either non-selective, for example, a clear glass, or selective, for example, an optical filter. Apparatus 10 comprises a light deflector 12, which serves for deflecting light 14, so as to provide a deflected light beam 16 characterized by one or more wavelength-dependent angles, representing the wavelength of light 14. More specifically, when light 14 is monochromatic, the deflection angle corresponds to its wavelength, and when light 14 is multi-chromatic (i.e., having a plurality of wavelengths), deflector 12 disperses light 14 at a plurality of angles, each corresponding to one -wavelength or a range of wavelengths, according to a predetermined dispersion equation.

According to a preferred embodiment of the present invention, deflector 12 may be manufactured as grating, such as, but not limited to, linear diffraction grating or linear reflection grating. The grating can be transmission grating or reflection grating, of any type, such as, but not limited to, acousto-optic grating, electro-optic grating and photorefractive grating. Generally, gratings are known to allow both redirection and transmission of light. The angle of redirection, or, more specifically, the dependence of the angle on the wavelength of the light, is determined by an appropriate choice of the period of the grating often called "the grating equation." Furthermore, the diffraction efficiency controls the energy fraction that is transmitted at each strike of light on the grating. Thus, in this embodiment, the predetermined dispersion equation is the grating equation of the grating, which relates the wavelength, λ, of light 14 to the deflection angle, β.

Representative example of a grating equation is given in Equation 1, below:

$$m\lambda = d\sin\alpha + d\sin\beta, \quad (EQ. 1)$$

where d is the grating period, α is the angle of entry of light 14 into the grating and m is the diffraction order, also referred to as spectral order, which is an integer. According to a preferred embodiment of the present invention, the diffraction order, m, and the grating period, d, are selected such that the absolute value of the ratio mλ/d is relatively small, say 2. One would appreciate that m=0 immediately satisfies this requirement. It is to be understood that other values of m and d are within the scope of the present invention, for example, for a wavelength ranging from infrared to ultraviolet, and a diffraction order of 1, the grating period may be between 500 and 2000 lines per mm. In the literature, the grating equation is often written as:

$$Gm\lambda = d\sin\alpha + d\sin\beta, \quad (EQ. 2)$$

where G is defined as 1/d and referred to as groove frequency, groove density, grooves per millimeter or pitch.

Alternatively, in another embodiment, deflector 12 may be manufactured as a prism, a mini-prism or a set of mini-prisms, all of which are known to deflect different wavelengths of light at different angles. In still another embodiment, deflector 12 can be a combination of grating and prism or any other optical element capable of deflecting light 14 at one or more wavelength-dependent angles. Optionally and preferably, apparatus 10 may comprise at least one anamorphic prism 15, positioned m the light path of light 14 (prior to the impingement on deflector 12) and/or in the light path of light 16 (after exiting deflector 12). An anamorphic prism is a device which allows for the magnification of a beam size along one axis while leaving the beam unchanged along another other axis. A combination of anamorphic prisms can control the magnification of the beam size in both axes. Thus, according to a preferred embodiment of the present invention, one or more anamorphic prisms 15 are positioned in the light path of light 14 or light 16 so as to control the spot size thereof. For example, anamorphic prism(s) 15 may positioned in the light path of light 14 so as to reduce the spot size on deflector 12 and in the light path of light 16 so as to increase the spot size after exiting deflector 12. This configuration has the advantage of increasing the angular effect generated by deflector 12, which, as further detailed hereinunder, is preferably exploited for improving analysis of the light.

In any event, as will be appreciated by one ordinarily skilled in the art, the knowledge of the deflection angle can be used to obtain at least a rough estimation of the spectral components of light 14. For example, when deflector 12 is a grating, a rough estimation of the spectral components of light 14 can be extracted from Equations 1 or 2.

Figure 2:
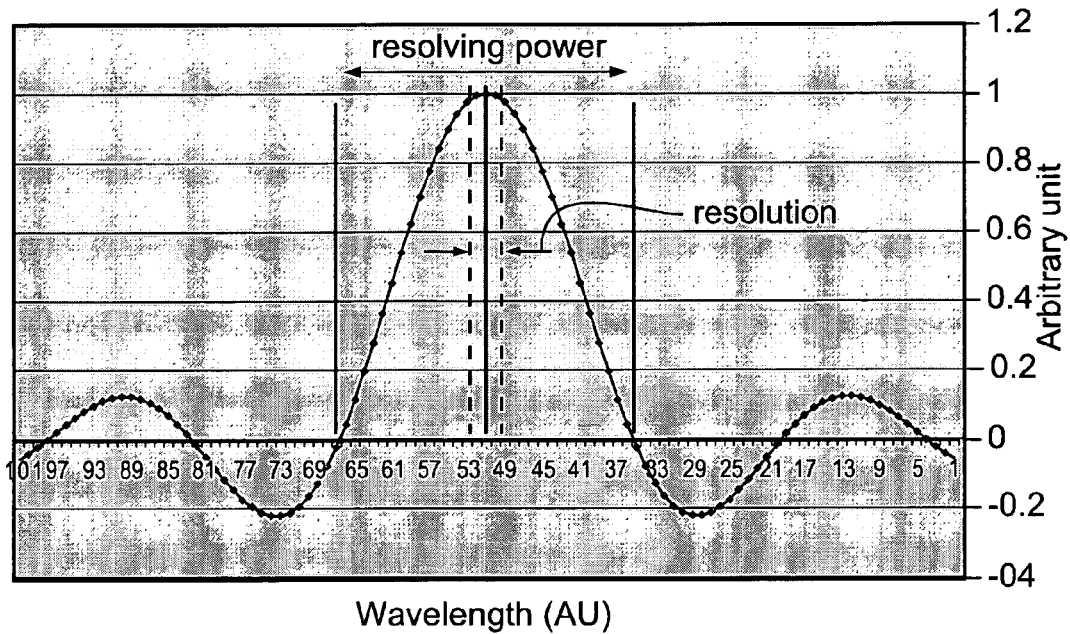
FIG. 2 shows a resolving power and a resolution for a typical wavelength measurement result in arbitrary units, according to a preferred embodiment of the present invention.

The resolving power, R, of an optical element which is used to measure wavelengths or separate light into its spectral components is defined as the ratio between the wavelength, λ, to the resolution of the particular optical element. Formally, R can be written as:

$$R = \lambda/\Delta\lambda, \quad (EQ. 3)$$

where Δλ is the resolution of the optical element. The resolving power and the resolution for a typical wavelength measurement result in arbitrary units are shown in FIG. 2. For grating, the resolution power, R, can be written in the form:

$$R = |W(\sin\alpha + \sin\beta)/\lambda| < 2\ W/\lambda \quad (EQ. 4)$$

where W is the ruled width of the grating. Thus, the maximal attainable resolving power of a commonly used grating is, two times the ruled width per unit wavelength of the grating.

While conceiving the present invention it was hypothesized, and while reducing it to practice it was realized that the resolving power of apparatus 10 can be significantly increased when deflected light beam 16 is polarized according to its angular dispersion. Thus, according to a preferred embodiment of the present invention apparatus 10 further comprises an encoder 20, which encodes the wavelength-dependent angle into light 16 in terms of polarization state thereof. The polarization state of the light is determined by the angle, which indirectly represents the wavelength of the light. Encoder 20 thus provides an encoded light beam 22, characterized by one (for a monochromatic light) or more (for a multi-chromatic light) angle-dependent polarization states, which respectively correspond to the wavelength-dependent angle. In the embodiment in which anamorphic prism 15 in employed, the spot size of light 16 on encoder 20 is changed, preferably enlarged, so as to optimize the angular dispersion of light 16 in encoder 20 thereby to optimize its capability to encode a different polarization state to each wavelength-dependent angle of light 16.

Encoder 20 preferably provides the angle-dependent polarization state by generating at least one angle-dependent polarization phase-shift. As further detailed hereinafter, the light may pass through encoder 20 more than one time, say, two, three or more times. For example, the light may pass through encoder two times: a first time before entering deflector 12 and a second time after being deflected thereby. This may be done, for example, by using two encoders, a first encoder, designated 20' in FIG. 1b, in the light path of light 14, prior to its impingement on deflector 12 and a second encoder, designated 20 in FIG. 1b, in the light path of light 16, after it exits deflector 12. Alternatively, a single encoder can be used, whereby the light is redirected such that it passes through encoder 20, deflected by deflector 12 and then redirected back into encoder 20.

The use of more than one encoder, or more then one pass of the light through a single is particularly useful when it is desired to achieve small (e.g., zero) polarization phase-shift for the central wavelength of deflected light beam 16 at a wide variety of angles incident on the grating.

According to a preferred embodiment of the present invention the sensitivity of encoder 20 is selected so as to maximize the generated polarization phase-shift. In other words, encoder 20 is characterized in that small differences in the deflection angle preferably correspond to large polarization phase-shift. As a representative example, for wavelengths of about 1550 nm and angular resolution of about 2 milliradians per nm, encoder 20' preferably generates a polarization phase-shift which is from about 0.05 radians to about 0.1 radians per 50 pm.

The value of the polarization phase-shift can be controlled by a judicious selection of the parameters of encoder 20. For example as further detailed hereinunder, in one embodiment encoder 20 is characterized by two indices of refraction: an ordinary index of refraction and an extraordinary index of refraction. These indices of refraction can be selected so as to obtain the desired value of the polarization phase-shift. The polarization phase-shift can also be wavelength-dependent, so that different wavelengths acquire different polarization phase-shift, whereby the sensitivity of the polarization phase-shift to the wavelength is larger is at lower wavelengths and smaller at higher wavelengths. For example, for a wavelength of about 400 nm, the polarization phase-shift is preferably from about 0.05 radians to about 0.1 radians per 10 pm. Another parameter which can affect the polarization phase-shift is the thickness of encoder 20. For a given wavelength, the sensitivity of the polarization phase-shift to the wavelength increases with the thickness of encoder 20. A typical thickness of encoder 20 is from about 5 nm to about 10 nm.

According to a preferred embodiment of the present invention any optical element which is capable of converting angular dispersion to a polarization state can be used as encoder 20. One such element is an optical crystal, for example, an anisotropic optical crystal, generally referred to herein as a geometrical crystal filter. Broadly speaking, the geometrical crystal filter operates as follows.

When entering the geometrical crystal filter, an incident light ray of arbitrary polarization splits into two separate light rays, called the ordinary ray and the extraordinary ray, each propagating within the crystal at its own velocity and with a polarization defined by the crystal symmetry. The propagation velocity of each ray is inversely proportional to the respective refractive index which characterizes the directions of propagation.

This bifurcation of the incident light ray leads to different optical paths hence also to a phase difference between the two rays. A geometrical crystal filter is characterized by an optical activity tensor which contains the relation between the refraction index, experienced by a particular light ray, and the impinging angle of the light ray on the crystal. The refraction indices of the crystals are referred to in the literature as the extraordinary refraction index and the ordinary refraction index. As different impinging angles correspond to different rotations of the polarization plane, the geometrical crystal filter thus induces an angle-dependent polarization state on each light ray arriving thereat.

Encoder 20 may be any birefringent or optically active crystal, either an on-axis crystal or an off-axis crystal. Combination of several, identical or different, crystals is also contemplated. For example, in one embodiment, encoder 20 is a slightly off axis optical crystal in which the light is passing at an angle close to its axis.

The polarization phase-shift, $\Delta\Phi$, generated by encoder 20, in the embodiment in which a single crystal is used, is given:

$$\Delta\Phi = [2\pi\Delta n\, L/(n_o\lambda)]\theta_0^2, \quad (EQ.\ 5)$$

where $\Delta n$ is the birefringence in the crystal (the difference between the extraordinary refraction index and the ordinary refraction index), L is the total aggregate length of crystal(s) in mm, $n_o$ is the ordinary refraction index and $\theta_0$ is the impinging angle of the central wavelength, in radians, relative to the system optical axis.

It is to be understood, that the form of Equation 5 is for the purpose of providing a transparent description of the present embodiment and is not intended to be limiting. Although Equation 5, in its present form is derived for a single crystal, an equivalent equation, or a set of equations can be constructed by one ordinarily skilled in the art for more than one crystal, by considering compensation of the angular dependence due to the transmission of light through more than one crystal.

For a small angular change around an angle $\theta_0$ the difference of the polarization phase-shift is given by the derivative of Equation 5 with respect to $\theta_0$:

$$\Delta\Phi' = 2[2\pi\Delta n\, L/(n_o\lambda)]\Delta\theta\theta_0. \quad (EQ.\ 6)$$

The angle equivalent to a single free spectral range is thus given by:

$$\theta_1 = \tfrac{1}{2}[(n_o\lambda)/(2\Delta n\theta_0 L)]. \quad (EQ.\ 7)$$

To a good approximation, in the wavelengths range of interest, the variations of $1/\lambda$ as well as the angle difference caused by these variations are small. In this approximation, Equation 6 can be written as:

$$\begin{aligned}
\Delta\Phi' &= -[4\pi\Delta nL/(n_o\lambda_0)]\Delta\theta\theta_0 \\
&= -[4\pi\Delta nL/(n_o\lambda_0)]\theta_0 u\Delta\lambda \\
&= B(\lambda_0 - \lambda) + const.
\end{aligned} \quad (EQ.\ 8)$$

where u is the dispersion provided by deflector 12, and the coefficient B is defined as $4\pi\,\Delta n\, L\, u\, \theta_0/(n_o\lambda_o)$. As a representative numerical example of Equations 5-8, a calcite crystal is considered, although, as stated, other optical crystals can also be used. Hence, for calcite crystal $\Delta n/n_o = 0.11$. Considering a crystal length, L, of about 20 mm, a wavelength, $\lambda$, of about 0.6 μm and an impinging angle, $\theta_0$, of about 0.1, then the single free spectral range angle, $\theta_1$ is about 0.68 milliradians. This value is to be compared with typical values of $\Delta\theta$ which are of order of a few milliradians per nanometer. For a typical dispersion of about 2 milliradians per nanometer and the above numerical values of $\Delta n$, L, $\theta_0$, $n_o$ and $\lambda_o$, the value of B is about 9 radians per nanometer, which is about three orders of magnitude above the aforementioned typical value of $\Delta\theta$. The reason for the large difference is the typically large birefringence of the crystal. The typical attainable polarization phase-shift, according to a preferred embodiment of the present invention, is therefore large, allowing apparatus 10 to perform an accurate analysis of the light.

According to a preferred embodiment of the present invention, for a better performance of the geometrical crystal filter, the light, on entry, preferably has a global polarization state which preferably does not depend on the deflection angle. This can be achieved, for example, by separating the beam of light into two channels using a beam splitter 21. Any suitable beam splitter can be used, including, without limitation, a double refraction plate.

Alternatively, a global polarization can be achieved using a polarizer 23 (see FIG. 1c), which can be, for example, a Wollaston prism or any other optical device capable of polarizing the light. This embodiment is also useful when apparatus 10 is used for Raman emission. As Raman emission is typically polarized, polarizer 23 selectively transmits only Raman emission and prevents reflected light from coming through.

Optionally, when the incoming is polarized in an arbitrary direction, apparatus 10 preferably comprises a depolarizer 25

(not shown, see FIG. 3) positioned before polarizer 23 for depolarizing the light prior to the polarization performed by polarizer 23.

Still optionally, apparatus 10 preferably comprises at least one polarization rotator 27 (see FIGS. 1b-c), designed and configured so as to rotate the polarization of light beam 16 and/or light beam 22. This embodiment is useful, for example; when it is desired to obtain a predetermined relative angle between the orientation of the polarization plane of light 16 (in the embodiment in which light 16 is polarized, e.g. by polarizer 23) and the axis of encoder 20.

Broadly speaking a polarization rotator receives a beam of radiation of any arbitrary polarization angle and produces a new beam, preferably coaxial with the incident beam, having a specified new polarization angle. Any optical device capable of rotating the polarization plane of the light can be used.

For example, in one embodiment, polarization rotator 27 is formed of an optically active medium, whereby the rotation of the polarization plane of the light depends on the thickness of the medium. In this embodiment, a rotation of the polarization can be achieved by two quarter waveplates. A quarter waveplate is a plate of optically material having a thickness such that there is a phase difference of a quarter of a wavelength (or some multiple quarters of wavelength) between the incoming beam and the outgoing beam so that when a linearly polarized bean enters the quarter waveplate, a circularly polarized bean exits, and when a circularly polarized bean enters the quarter waveplate, a linearly polarized bean exits. When a linearly polarized beam enters two quarter waveplates, a first quarter waveplate generates a circular polarization and a second quarter waveplate generate a linear polarization. In such configuration, because the light exiting the first quarter waveplate is circularly polarized, the second quarter waveplate can be oriented in any direction, and, in particular, in such direction that the polarization of the light is transformed from a circular polarization to a linear polarization in the desired direction.

Representative examples of polarization rotators which can be used include, without limitation, a crystal quartz polarization rotator, a reflective polarization rotator, a fast switching liquid crystal polarization rotator and the like.

One of ordinary skill in the art will appreciate the difference between encoder 20 and other commonly employed methods of detecting angular dispersion, such as, the optical triangulation method. In the optical triangulation method, the angular dispersion is converted into a position whereas in encoder 20 the angular dispersion converted into a polarization phase-shift. A major drawback of the optical triangulation method is that some kind of discretization has to be employed in order to measure the position to which the angular dispersion is converted. This discretization is often achieved by a detector array having a plurality of pixels, where each pixel integrates the fight impinging on its entire surface, without consideration to the sub-pixel position. Such approach creates an electrical signal which depends on the total energy. Due to this discretization any direct information relative to sub-pixel position is lost, and the possibility to perform sub-pixel precision is very limited. According to a preferred embodiment of the present invention, no discretization procedure is required in encoder 20, so that the measurement precision is limited solely by the signal to noise ratio.

An additional known optical element for generating a polarization phase-shift is birefringent filter. Like the aforementioned geometrical crystal filter, birefringent filters also have the property that their refractive index, hence the velocity of propagation of light therethrough, varies with the propagation direction through the filter. In a birefringent filter the index of refraction builds a huge polarization phase-shift, the value of which is very sensitive to the wavelength. Because of the large sensitivity of the generated polarization phase-shift to the wavelength, systems which incorporate birefringent filter are known to be unstable in terms of sensitivity of the system to external conditions. Such filters can therefore be used only in stable environments such as research laboratories.

In encoder 20, on the other hand, the polarization phase-shift is preferably used to discriminate small angular differences. According to a preferred embodiment of the present invention encoder 20 is calibrated so as to generate a zero or small polarization phase-shift for a predetermined set of wavelengths and a non-zero polarization phase-shift for wavelengths other than said predetermined set of wavelengths. The predetermined set of wavelengths preferably comprises a central wavelength and a repetitive set of wavelengths being associated therewith. This repetitive set of wavelengths may include any number of discrete wavelengths, i.e., one, two or more wavelength, depending on the specific application for which apparatus 10 is designed. The repetitive set can also be time dependent, so that at different times a different set of wavelengths are associated with a small or zero phase-shift.

The advantage of this embodiment is the substantial reduction of sensitivity of apparatus 10 to external conditions. More specifically, by calibrating encoder 20 to a zero (or substantially small) polarization phase-shift at the central wavelength, the range of available polarization phase-shift is reduced so that even rather large environmental variations preferably lead to relatively small polarization phase-shift variations.

The polarization phase-shift, which, as stated, is a function of the impinging angle of the light, has an additional advantage over prior art systems. A severe limitation in prior art systems is that, prior to any attempt to measure the spectral components of the light, a full collimation of the beam is required. This is because the light source emitting the light typically includes a narrow slit which generates considerable diffraction effects. Such collimation significantly reduces the amount of achievable energy and increases the length and the total weight of the system. Furthermore, the diffraction effects often reduce the measurement accuracy.

According to a preferred embodiment of the present invention the polarization phase-shift, as provided by encoder 20, is used in order to minimize or eliminate diffraction effects which are caused by the slit. Nevertheless, collimation of the light is not excluded and, in some embodiments of the present invention, apparatus 10 further comprises a collimator 26. Collimator 26 may serve for collimating light 14, prior to its impingement deflector 12, or for collimating encoded light beam 22 after being encoded by encoder 20. When light 14 is emitted from source 13, collimator 26 preferably comprises an objective 17 and an aperture 19 (see FIG. 1c).

Apparatus 10 further comprises a decoder 24. Decoder 24 uses the polarization state(s) of encoded light beam 22 and determines the spectral components of light 14. According to a preferred embodiment of the present invention decoder 24 converts the information extracted from beam 22 to electrical signal which can subsequently be processed by a data processor 18. As further detailed hereinunder, there is more than one way by which decoder 24 can decodes the polarization states of encoded light beam 22. In any event, because, as stated, the polarization states of beam 22 depend on the angles, the knowledge of the polarization states of beam 22 allows the determination of the angles which in turn allow the determination of the spectral components of the light.

According to a preferred embodiment of the present invention decoder 24 splits encoded light beam 22 into two secondary polarized light beams, from which a contrast function can be calculated. One ordinarily skilled in the art will appreciate that such contrast function is proportional to the polarization state of beam 22.

Alternatively, in another embodiment, decoder 24 preferably generates a representative time-delay for each polarization state of beam 22. Subsequently the timed-delay is preferably used for determining the polarization state of beam 22. According to the presently preferred embodiment of the invention decoder 24 comprises a temporal polarization phase-shifter 28 which accumulates a time-dependent polarization phase-shift to encoded light beam 22. Polarization phase-shifter 28 preferably communicates with an external clock (not shown), to facilitate the time-dependence of the polarization phase-shift accumulated thereby. Representative examples of temporal polarization phase-shifters which can be used include, without limitation, a liquid crystal light valve and a single- or multi resonance piezoelectric crystal, which may be, for example, cubic crystal, triagonal crystal, hexagonal crystal and the like. Representative examples of piezoelectric crystal materials include, without limitation, GaAs, ZnSe, quartz, lithium niobate and lithium tantalate.

According to a preferred embodiment of the present invention the additional, time-dependent, polarization phase-shift which is added to the polarization phase-shift of beam 22 has a periodic form. For example, in the embodiment in which temporal polarization phase-shifter 28 is a crystal valve, being under a potential difference, V, the overall polarization phase of beam 22, denoted $p_v$, is preferably:

$$p_v = p + aV\cos(\omega t), \quad (EQ. 9)$$

where a is a valve-dependent coefficient, $\omega$ is the clock's frequency, and p is referred to hereinafter as a pseudopahse and represents the polarization phase-shift, in units of frequency, prior to the operation of temporal polarization phase-shifter 28. According to a preferred embodiment of the present invention the pseudopahse has a slow or no time-dependence, comparing to the inverse of the clock's frequency, $\omega$. In terms of the frequency, f, which is inversely proportional to the wavelength, $\lambda$, the pseudopahse, p, can be written in the form (see also Equation 8):

$$p = p_0 + b(f - f_0), \quad (EQ. 10)$$

where $f_0$ is an arbitrary reference frequency and b is the frequency representation of the aforementioned B. As further detailed hereinbelow, the coefficient b (or B, when the equations are written in the wavelength representation), preferably serves as a system-parameter, through which the information constituted by the light can be extracted.

According to a preferred embodiment of the present invention, phase shifter 28 is characterized by more than one resonance frequency, in which case Equation 9 includes more then one term, each corresponding to a difference resonance. In this embodiment, the overall intensity, I, of the light as a function of time, t, can be symbolically written as:

$$I(t) \sim \Sigma_{n,m} c_{nm} \cos(n\omega_1 t + m\omega_2 t) J_n(a_1) J_m(a_2), \quad (EQ. 11)$$

where $c_{nm}$ are expansion coefficients, $a_1, a_2$ are related to the voltages on phase shifter 28 and $J_n, J_m$ are Bessel functions of order n, m, respectively. This embodiment is particularly useful when the analysis of light 14 is combined with a low-resolution as further detailed hereinbelow.

Figure 3:
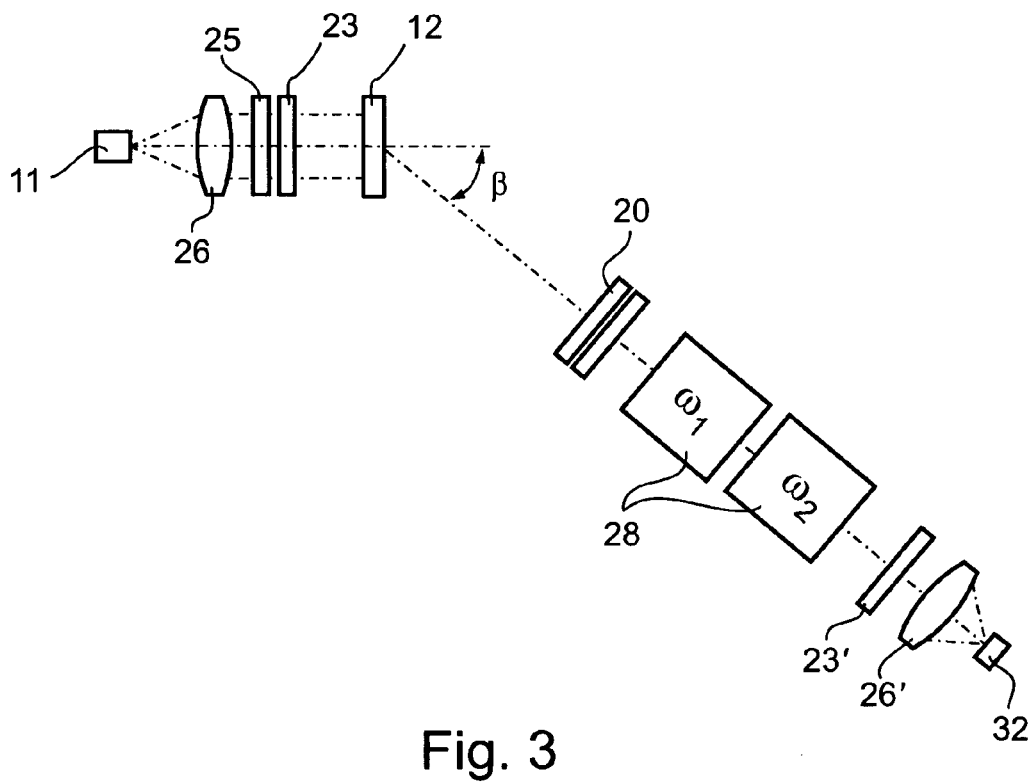
FIG. 3 is a simplified illustration of the apparatus of FIGS. 1a-c, in a typical configuration in which more than one resonance frequency is employed, according to a preferred embodiment of the present invention.

A typical configuration, in which phase shifter 28 is characterized by more than one resonance frequency is shown in FIG. 3. In the preferred embodiment illustrated in FIG. 3, the light is collimated by collimator 26, polarized by polarizer 23, deflected by deflector 12 to an angle, and encoded by encoder 20, as further detailed hereinabove. Subsequently, the light passes through polarization phase-shifter 28 which preferably comprises two crystal valves, of characteristic frequencies $\omega_1$ and $\omega_2$, and polarized again, by an additional (global) polarizer 23'. Optionally and preferably, the light is collimated again, using an additional collimator 26'.

According to a preferred embodiment of the present invention encoder 20 and polarization phase-shifter 28 are preferably selected such that the output for specific harmonics is substantially independent of the component at specific frequencies, so that the sensitivity of the data to certain frequencies is enhanced relative to the sensitivity of the data to other frequencies. This embodiment is particularly useful when the number of spectral components of the light is not large. For example, in Raman emission, encoder 20 and polarization phase-shifter 28 can be selected such that there is no, say, first-harmonic response from polarization phase-shifter 28. Then, any first-harmonic response is due to the presence of Raman lines.

Referring now again to FIGS. 1a-c, according to a preferred embodiment of the present invention decoder 24 further comprises a polarization phase-shift analyzer 30, which analyzes the time-dependent polarization phase-shift and provides an optical signal with a time-dependent intensity. One of ordinary skill in the art would appreciate that the light may enter analyzer 30 either directly (FIGS. 1a-b) or using an appropriate mirror 31 (FIG. 1c), which redirect the light into analyzer 30. The time-dependent intensity can then be converted to electrical signal, e.g., using one or more optical converters 32 (see also FIG. 3). Representative examples of optical converters which are contemplated, include, without limitation, charge coupled devices, CMOS detectors, photovoltaic detectors, pin detectors, photodiodes, charge injection devices, image intensifiers, photoconductor detectors, avalanche detectors, photomultipliers or any combination of such or similar devices.

In the embodiment in which more than one optical converter 32 is used (FIGS. 1b-c), each optical converter 32 can be used to convert a separate portion of the spectrum. This embodiment is particularly useful when apparatus 10 is uses for analyzing light having more than one wavelength, for example, when apparatus 10 serves as a multi-wavelength meter or a spectrograph, as further detailed in the Examples section that follows. According to a preferred embodiment of the present invention apparatus 10 comprises a polarization beamsplitter 33 which separate the beam into two different polarization beams, a first polarized beam 22a and a second polarized beam 22b each directed into a different optical converter. Optionally and preferably one or more lenses 35 are positioned in the optical path of beams 22a and 22b for further collimation prior to the conversion to electrical signal.

One of ordinary skill in the art would appreciate that the analysis of the light can be obtained using a mathematical inversion procedure. Representative examples of appropriate procedures which may be employed by decoder 24, are further detailed hereinbelow.

Hence, generally, decoder 24 uses a signal (optical or electrical) which represents an integrated intensity over the frequency (or wavelength in the wavelength representation). Such signal depends, inter alia, on b or B, the aforementioned frequency representation and wavelength representation "system-parameters." According to a preferred embodiment of the present invention the signal is sampled a sufficient number of times, each time with a different value of b or B, so as to span a discrete basis of signals in the system-parameter space. It is to be understood, that although the following description is for a single system-parameter, the use of more than one, say, two, three or more system-parameters, is not excluded from the scope of the present invention. The number of the samples, and correspondingly the number of known values of b or B is preferably selected such that the signal can be transformed, by an appropriate mathematical transform, from the frequency or wavelength space to the system-parameter space.

A preferred number of samples is, without limitation, above 5 samples, more preferably above 64 samples, most preferably above 1000 samples. Mathematically, the integrated signal used by decoder 24 can be expressed, in the frequency representation, as:

$$U(b,t)=\int \cos(p(t)+bf)I(f)df,\qquad\text{(EQ. 12)}$$

where p(t) is a time-dependent polarization phase, which can be, for example, overall polarization phase, $p_v$, given by Equations 9-10.

According to a preferred embodiment of the present invention, the integrated signal of Equation 12 is preferably expressed as a complex function having a real part and an imaginary part. This can be done in more than one way. In one embodiment, two different values of p(t) are applied, for example, p(t)=0, representing a real part of the signal, and p(t)=π, representing an imaginary part of the signal.

In another embodiment, light bean 22 is split into two parts, a first part, undergoing no polarization phase change, represents the real part of the signal, and a second part, undergoing a polarization phase addition of, say, a quarter of a cycle (π/2), represents the imaginary part of the signal.

In an additional embodiment, p(t) has a periodic time-dependence with a constant frequency, π, for example, p(t)=A cos(ω t). Substituting into Equation 12, the signal can be written as:

$$U(b,t) = \int \cos(A\cos(\omega t)+bf)I(f)df \qquad\text{(EQ. 13)}$$
$$= \sum_n J_{2n}(A)\cos(2n\omega t)\int \cos(bf)I(f)df +$$
$$\sum_n J_{2n-1}(A)\cos(2n-1)\omega t)\int \sin(bf)I(f)df,$$

where the first sum of Equation 13 represents the real part of the signal, and the second sum of Equation 13 represents the imaginary part of the signal.

In any event, the integrated signal of Equation 12 is thus expressed as a complex function which, in an exponential form, can be written as:

$$U_{exp}(b)=\int \exp(ibf)I(f)df,\qquad\text{(EQ. 14)}$$

where $i^2=1$.

I(f), namely, the intensity as a function of the frequency (or equivalently the intensity as a function of the wavelength) can thus be extracted by collecting a sufficient number of samples of $U_{exp}$, for different values of the system-parameter b. This can be done, as stated, by a mathematical transform, such as, but not limited to, a Fourier transform, a Gabor transform, a Haar transform, a Hartley transform, a sine transform, a cosine transform, a Hadamard transform and a wavelet transform. For example, when a Fourier transform is used, according to a preferred embodiment of the present invention, the intensity is given, in the frequency representation, by:

$$I(f)=\text{const.}\int \exp(-ibf)U_{exp}(b)db.\qquad\text{(EQ. 15)}$$

The use of a mathematical transform is particularly useful when the number of known values of system-parameters is large. For small number of known values of system-parameters, other mathematical procedures can be used.

Hence, in one embodiment, the intensity is preferably extracted using a linear prediction method and its derivatives. One such method is know as the Prony's method, in which the intensity is extracted by harmonic inversion of $U_{exp}(b)$. Specifically, assuming that I(f) can be written in the following form:

$$I(f)=\Sigma_n d_n/(f-w_n),\qquad\text{(EQ. 16)}$$

where $d_n$ and $w_n$, n=1, 2, . . . are sets of complex numbers. $U_{exp}(b)$ is then given by:

$$U_{exp}(b)=\int \exp(ibf)I(f)df\qquad\text{(EQ. 17)}$$

which can be written as:

$$U_{exp}(b)=\text{const}\,\Sigma_n d_n \exp(iw_n b).\qquad\text{(EQ. 18)}$$

It will be appreciated that in this embodiment, the extraction of I(f) is equivalent to the extraction of $d_n$ and $w_n$ from $U_{exp}(b)$, which is the purpose of the linear prediction method. Alternatively, the intensity can be extracted using any of the methods known in the literature for extracting spectral information, or performing harmonic inversion, from a short-length signal, such as, but not limited to, a maximum entropy or a linear prediction method.

For example, in the embodiment in which the intensity is extracted using the maximum entropy method, I(f) can be extracted either directly by inversion or indirectly by first assuming a specific form therefor.

It is appreciated that the scope of the present invention is not limited to maximum entropy or linear prediction, and that any other known method can be used. To this end see, e.g., Numerical Recipes (www.nr.com).

In an additional embodiment, particularly useful when a rough estimate of the positions of the spectral lines of light 14 is known, I(f) is expanded in terms of the known spectral lines and a least-square fitting is performed to determined the coefficient of the expansion.

There is more than one way to sample the signal, U, at different values of b or B. Preferably, the measurement described in the above embodiment is repeated a plurality of times, each time with different value of the system-parameter (either b or B), using a mechanism 34 for varying the system-parameter, which may be embodied in more the one way, as further detailed hereinunder. The variation of the system-parameter can be done in any physical dimension, including, without limitation, lateral dimension, angular dimension, time or any combination thereof. The dimension by which the system-parameter is varied is preferably selected so as to optimize both the smoothness and the sensitivity of the signal U. More specifically, the system-parameter is varied so as to obtain a substantially smooth and continuous signal. The smoothness of the signal can be defined, for example, by a substantially continues first derivative. Following are several examples of methods of varying the system-parameter, according to preferred embodiments of the present invention.

Broadly speaking, the variation of the system-parameter can be achieved by varying any variable on which the system-parameter depends. For example, referring to Equation 8, because the polarization phase-shift in the wavelength representation, $\Delta\Phi'$, is proportional to the system parameter, $B=4\pi\Delta n \, L \, u\theta_0/(n_o\lambda_0)$, any variation of $\Delta n$, L, u, $\theta_0$ and/or $n_o$ results in a variation of B. Equivalent expression can be made by a person of ordinary skill in the art in the frequency representation for b.

Hence, in one embodiment, the system parameter is varied by further deflecting light beam 16, for example, using a rotating mirror 36, positioned in the optical path of the light for example, between deflector 12 and encoder 20, or between light source 13 (or optical fiber 11) and deflector 12. Preferably the additional deflection is time-dependent so that the polarization phase-shift varies with time.

In other embodiments, the system parameter can be varied by certain dynamical operations performed on encoder 20. These embodiments are further detailed herein below, with reference to FIGS. 4a-c, which are simplified illustrations of encoder 20 in the embodiments in which encoder 20 is a geometrical crystal filter 38.

Figure 4A:
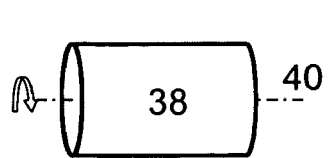
FIGS. 4a-c are schematic illustrations of a geometrical crystal filter, according to a preferred embodiment of the present invention.

Hence, Referring to FIG. 4a, according to a preferred embodiment of the present invention the system parameter is varied by rotating geometrical crystal filter 38 about an axis 40, so as to vary the angle-dependent polarization phase-shift. In this embodiment, polarization rotator 27 (in the embodiment in which it is employed) is preferably constructed such that a substantially constant relative angle between the orientation of the polarization plane of light 16 and the axis of geometrical crystal filter 38 is maintained. Additionally, a second polarization rotator 27' is preferably employed in a manner such that a substantially constant relative angle between the orientation of the polarization plane of light 22 and the axis of phase-shifter 28 is maintained. The advantage of this embodiment is that the efficiency by which decoder 24 extracts the information from light 22 can be optimize, substantially without a specific dependence on the orientation of geometrical crystal filter 38. For example, a skilled artisan will appreciate that when the orientation of the polarization plane of light 22 matches the axis of geometrical crystal filter 38, a more accurate mathematical transform can be obtained.

According to a preferred embodiment of the present invention polarization rotators 27 and 27' are designed and constructed such that rotator 27 rotates the polarization of light beam 16 from a first polarization orientation to a second polarization orientation, and rotator 27' rotates the polarization of light beam 22 from the second polarization orientation to the first polarization orientation, whereby the second polarization orientation substantially equals the orientation of geometrical crystal filter 38.

This can be done in any way known in the art for rotating the polarization plane of the light. For example, in the embodiment in which rotator 27 is formed of two quarter waveplates, a first quarter waveplate can be at a fixed orientation, so as to temporarily transform the polarization of light 16 from a linear polarization to a circular polarization, and a second quarter waveplate can rotate with geometrical crystal filter 38 (e.g., by attaching it thereto) so as to transform back the temporarily circular linear polarization of light 16 to a linear polarization in an orientation parallel to the axis of geometrical crystal filter 38. Similarly, when second polarization rotator 27' is formed of two quarter waveplates, a first quarter waveplate thereof can rotate with geometrical crystal filter 38 so as to temporarily transform the polarization of light 22 from a linear polarization to a circular polarization, and a second quarter waveplate of rotator 27' can be at a fixed orientation, so as to transform back the temporarily circular linear polarization of light 22 to a linear polarization in an orientation parallel to the axis of phase-shifter 28.

It is to be understood, however, that the above description is not intended to limit the scope of the present invention, and that in any of the embodiments in which apparatus 10 is employed, apparatus 10 can operate with or without the aforementioned polarization rotator(s).

Figure 4B:
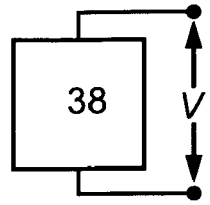
Figure 4C:
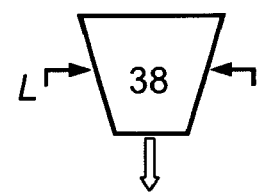

Referring to FIGS. 4b-c, in an alternative, yet preferred embodiment, the effective length, L, of geometrical crystal filter 38 may be varied, so as to vary the polarization phase-shift. This can be done, either electrically, for example, by using an electrooptic crystal as the geometrical crystal filter and applying a voltage thereon (FIG. 4b), or mechanically, by an appropriate selection of the shape of geometrical crystal filter 38 (FIG. 4c). More specifically, the shape of at least one geometrical crystal filter is preferably such that when a translational motion is applied thereto, its effective length is varied.

In another embodiment, the system parameter may be varied by varying the grating equation (see, e.g., Equations 1 and 2). This may be done, for example, by using a dynamic grating, characterized by a dynamic grating equation which can be modified (e.g., electrically or acoustically), or by using a grating which is characterized by a first grating equation in a first dimension and a second grating equation in a second dimension, so that, effectively, the grating equation varies with one of the dimensions.

In a further embodiment, the system-parameter may be varied using a spatial variable grating directly on geometrical crystal filter 38. The advantage of this embodiment is a smaller amount of elements which have to be assembled to apparatus 10.

It is to be understood that any combination of the above embodiments can be used so as to allow decoder 24 to accurately analyze light 14. As further detailed in the Examples section that follows, the analysis can be done both to a monochromatic light and to a multi-chromatic light. In any event, the analysis, as described above can be improved by combining it with a low-resolution analysis.

The advantage of combining the above analysis with a low-resolution analysis is that it allows a more precise measurement to be performed. This can be illustratively understood by an analogy to the two arms of a watch, where a low resolution arm measures the minutes and a higher resolution arm measure the minutes.

Figure 5A:
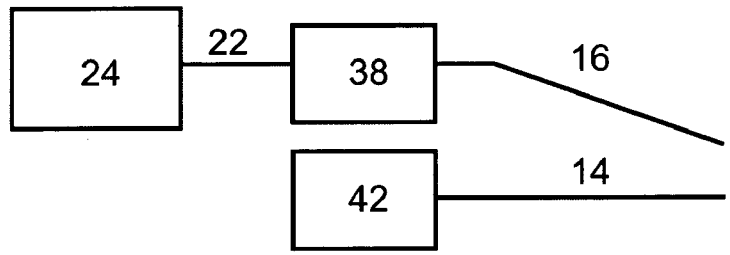
FIGS. 5a-c is a schematic illustration of the apparatus of FIGS. 1a-c, which comprises a low-resolution optical device, according to a preferred embodiment of the present invention.
Figure 5B:
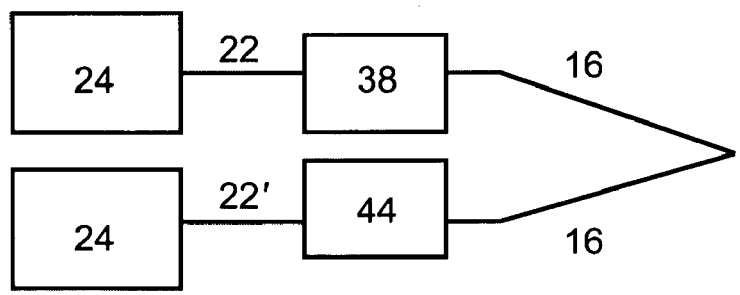
Figure 5C:
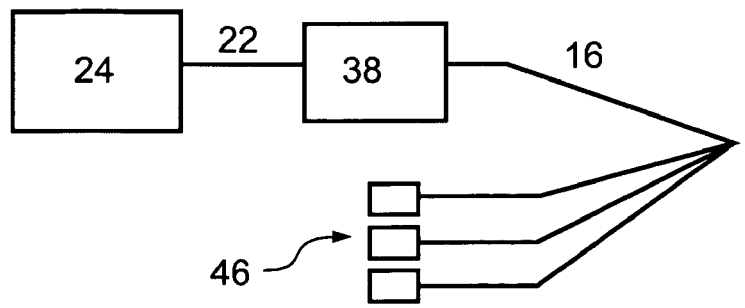

Reference is now made to FIGS. 5a-c, which are schematic illustrations of apparatus 10 which further comprises a low-resolution optical device 42, according to a preferred embodiment of the present invention.

Hence, referring to FIG. 5a, device 42 may be any device known in the art, capable of measuring the wavelength(s) of light 14. Representative examples include, without limitation a wavelength meter and a spectrometer. Thus, in this embodiment, a portion of light 14 is redirected into device 42 which provides a rough estimation of the wavelength of the light, and a second portion is directed into deflector 12 (not shown, see FIGS. 1a-c) and geometrical crystal filter 38 and decoder 24 as further detailed hereinabove.

Referring to FIG. 5b, in another embodiment, device 42 preferably comprise an additional geometrical crystal filter 44 having a free spectral range which is different (say, larger) than the free spectral range geometrical crystal filter 38. In this embodiment, a portion of light 16 passes through filter 38 and another portion passes through filter 44, so that to encoded light beams are formed, a high resolution beam and a low-resolution light beam, respectively designated 22 and 22' in FIG. 5b. Light beam 22 and 22' are then preferably decoded by one ore more decoders, similar to decoder 24, as further detailed hereinabove.

In another embodiment, shown in FIG. 5c, optical device 42 directly uses the wavelength-dependent angles so as to determine the low-resolution spectral range. This can be done, for example, using a position sensing device 46, whereby a position of deflected light beam 16 corresponds to a respective wavelength-dependent angle. Hence, in this embodiment, a portion of light beam 16 is not encoded, but rather directly detected by device 46, while the other portion of beam 16 is encoded by geometrical crystal filter 38 and subsequently decoded by decoder 24 as further detailed hereinabove.

It is to be understood, that device 42 can be used either in parallel, as illustrated in FIGS. 5a-c, or in serial, in which case device 42 is positioned after geometrical crystal filter 38. In case of parallel use, the light can be separated using any known optical device, such as, but not limited to, beam splitter 21 (not shown, see FIGS. 1a-c). Optionally and preferably, the separation of the light can be done by using higher diffraction orders. More specifically, as the deflection angle depends on the diffraction order, m, (see Equation 1 or 2), separation of the light is preferably achieved by and may be exploited by positioning device 42 in the light path of high diffraction orders.

Splitting of the input light can also be used for the purpose of performing an independent measurement as a reference channel. Thus, a small part of the light is preferably directed to phase shifter 28 and on to an optical converter, which converts the optical signal to an electrical signal. The electrical signal can then be used for assessing the effect of phase shifter 28 on the measurement's accuracy.

As stated, the light may pass through geometrical crystal filter 38 more than one time. For example, the light can pass through the filter 38 twice, a first time before deflector 12 and a second time after deflector 12. The advantage of this embodiment is that the angle and the grating mode are tailored such that that the polarization is substantially independent of the incoming physical angle. As the polarization angle (after passing through filter 38) is proportional to the impinging angle, the total polarization change after all passes through filter 38 is proportional to the sum of all the impinging angles (at each pass). For example, denoting the sine of the impinging angle prior to the first pass of the light through the crystal by sin θ', and the impinging angle prior to the second pass of the light through the crystal by sin θ, then for two passes, the total polarization is qualitatively proportional to sin θ'+sin θ.

As further detailed hereinbelow, the elimination or at least minimization of the sensitivity to the initial direction of light 14, can be achieved by passing the light through encoder 20 more than one time.

Reference is now made to FIGS. 6a-b, which are schematic illustration of apparatus 10 in the embodiment in which the light passes encoder 20 two times. As will be appreciated, this can be done either using two geometrical crystal filters or using a single geometrical crystal filter. Shown in FIGS. 6a-b are two geometrical crystal filters, referred to herein as an α-crystal 52 and an β-crystal 54, having properties similar to geometrical crystal filter 38, and grating 50. The polarization, $p_\beta$, accumulated to the light after β-crystal 54, can be written as:

$$p_\beta(\lambda-\lambda_0)+C(\theta-\theta_0), \quad \text{(EQ. 19)}$$

where C is characteristic to β-crystal 54 and grating 50. When the magnitude of the second term of Equation 19 becomes large, or, more precisely, has a large dispersion in its initial value, the dispersion is also large (of the order of π radians). According to a preferred embodiment of the present invention α-crystal 52 is so positioned to minimize this effect. Because the tight impinges on α-crystal 52 prior to the grating, for the corresponding polarization, $p_\alpha$, the first term of Equation 19, is suppressed, and can therefore be neglected:

$$p_\alpha = C'(\theta-\theta_0), \quad \text{(EQ. 20)}$$

where C' is a different coefficient, and the first term is missing. Thus, the position and characteristics of α-crystal 52 and β-crystal 54 are preferably selected so as to minimize the sum C+C', e.g., using a Littrow mode in which the light is reflected back substantially to the same direction from which it has arrived to the grating. The advantage of the presently preferred embodiment of the invention is that, by reducing the dependence of the polarization on the direction of the incoming light, allows apparatus 10 to analyze light without collimation, even when the light initially has large angular dispersion. It was found by the Inventors of the present invention that apparatus 10 is capable of analyzing light having large angular dispersion, preferably from 0 to milliradians, more preferably from 0 to 40 milliradians most preferably from 0 to 60 milliradians. It will be appreciated that the above description hold for any type of grating either reflection grating (see FIG. 6a) or transmission grating (see FIG. 6b).

The advantage of using transmission grating is that in transmission mode, there is no interference between the incoming light and the outgoing light. According to a preferred embodiment of the present invention, when transmission grating are used, grating 50 is formed on the face of one crystal, say, α-crystal 52, and β-crystal 54 is attached thereto, so that α-crystal 52, grating 50 and β-crystal 54 are essentially one component.

An additional advantage of the transmission grating is that a better control can be achieved on the value of the coefficients C and C', for example by varying the effective length of α-crystal 52, either electrically or mechanically as further detailed hereinabove with reference to FIGS. 4b-c. One of ordinary skill in the art would appreciate that the fine tuning of the effective length of α-crystal 52 is extremely useful for the purpose of eliminating the sum C+C'. An efficient control on the value of C' can also be achieved by varying the relative angle between α-crystal 52 and β-crystal 54, e.g., by rotating one or both of the crystals, as further detailed hereinabove. Other methods to control the value of C and/or C', include, without limitation (i) using a mirror to redirect the light, prior to the impinging on α-crystal 52 and/or the impinging on β-crystal 54; (ii) using a reflection grating which reflects light in one direction, and is uniform in the orthogonal direction so that the interfere between the incoming light and the outgoing light is eliminated, or at least minimized; and (iii) using grating in which the entrance angle is different than the and exit angle.

Apparatus 10 can be, employed in many applications, either as a wavelength meter or a spectrometer. Apparatus 10 enjoys many advantages exceeding similar prior art systems. As stated, in several embodiments, apparatus 10 can operate without collimation. This allows apparatus 10 to have a short focal length, thus to have small dimensions and low weight. In addition, apparatus 10 enjoys wide spectral range, preferably from infrared to ultraviolet, with high resolution, preferably sub nanometer resolution, more preferably sub picometer resolution. According to a preferred embodiment of the present invention a total analysis time of the light can be as short as about 1 millisecond, more preferably about 1 microsecond, most preferably about 1 nanosecond or less. It is to be understood that other the total analysis times are also contemplated, e.g., several seconds, several minutes, several hours and more. Thus, the time scales of apparatus 10 preferably range from sub-nanosecond scale to a few hours. Apparatus 10 is preferably characterized by a detectivity of from about −80 db or less to about −0 db or higher, more preferably from about −80 db to about −20 db, most preferably from about −80 db to about −40 db, say about −50 db, about −60 db, about −70 db or less.

As stated, apparatus 10 can collect data from large angles, so that only a small portion of the energy of the light is lost. Hence, apparatus 10 is extremely sensitive comparing to similar prior art devices. An additional advantage of apparatus 10 is the low bill of materials, of which apparatus 10 is made, and the overall low mechanical tolerance thereof.

Because the geometrical crystal filter and the grating are not sensitive to temperature, apparatus 10 is preferably athermal. Furthermore, the thermal dependence of the geometrical crystal filter, grating and the α-crystal is preferably arranged to yield small overall T-dependence.

The response rate of apparatus 10 is preferably similar to the response rate of a photoreceiver. This embodiment of the present invention can be exploited in numerous applications.

Hence, in one embodiment, apparatus 10 is preferably used for following laser changes. This embodiment is useful, for example, for stabilizing lasers by using a feedback loop, or for tracking changes due to environment or due to mode hopping.

In another embodiment, apparatus 10 is preferably used to follow pulses in time. In this embodiment, a slow voltage modulation of the resonance piezoelectric crystal is preferably employed so as to sweep the frequency spectrum and to fit specific lines. In this respect, apparatus 10 can also be used in regions where light spikes are obtained.

In an additional embodiment, apparatus 10 is preferably used in conjunction with modulating light sources, typically laser, so that the outgoing light has a component which is frequency modulated. This embodiment is useful, for example, for discriminating between Raman emission which is instantaneous and fluorescence and especially phosphorescence. In addition, this embodiment can be used for discriminating between background and emission-of-interest, or between different light sources (if more than one is present).

In still another embodiment, apparatus 10 is preferably used with modulating a laser at a frequency which is almost the same as the frequency of the resonance piezoelectric crystal. One ordinarily skilled in the art would appreciate that with such configuration, the harmonics of the overall electronic signal are mostly integer multiples of the small frequency difference between the laser and the resonance piezoelectric crystal, so that a larger number of harmonics can be collected, with high accuracy.

For example, the laser can be modulated, using the current of resonance piezoelectric crystal as the electrical reference, at a frequency $\omega_1 + d\omega$. With such modulating, a beat frequency can be detected at $d\omega$. Obtaining a beat at low frequency significantly improve the performances of many presently know light detectors, where the signal to noise ratio at low frequencies (from a few KHz to a few tens of KHz) is higher than at low frequencies (hundredths of KHz), due to inherent electronic limitation. An additional advantage of obtaining a beat at low frequency is that the source modulation reduces markedly the influence of additional light sources which may interfere with the process.

By modulation of one or more lasers, apparatus 10 can be used for multi-lasers test system. Each laser is modulated with its own frequency, so that by following the corresponding frequency and their harmonics one determines the polarization-dependent signal associated with each laser, thereby also the frequency of each laser. This is useful either for tracking specific lines or with a closed loop application, in correcting these lines.

In yet an additional embodiment, apparatus 10 is preferably used for generating frequency multiplexed signals whether the frequencies map a single or double lateral imaging dimensions. This can be done by an acoustooptical set-up as described in an article by W. T. Rhodes, entitled "Acousto-optic signal processing: convolution and correlation,", published in the Proceedings of the IEEE 1981 and in Selected Papers on Acousto-Optics, Adrian Korpel, Editor, SPIE MS16, June 1990, the contents of which are hereby incorporated by reference. Alternatively a matrix of resonating crystal can be used, as described by an article by N. Ben-Yosef and G. Y. Sirat, entitled "Real-Time spatial filtering utilizing the Piezoelectric-elastooptic effect," published in Optica Acta 29:419-423 (1982), the contents of which are hereby incorporated by reference. With such a scheme a full or partial imaging can be created using a small number of detectors.

In still an additional embodiment, apparatus 10 can be used as a sensor for sensing environmental conditions, such as, but not limited to, temperature, pressure, magnetic field and electric field. Being highly sensitive for small differences in wavelengths, any environmental change which affects the wavelength of the light can thus be monitored by analyzing the spectrum of the light. For example, vibrations of deflector 12 and/or encoder 20 results at least in small variations of the wavelength-dependent angle, provided by deflector 12, or the angle-dependent polarization state, provided by encoder 20. Thus, apparatus 10 can serve as a vibration sensor whereby the aforementioned variations represent vibrations.

It is expected that during the life of this patent many relevant optical crystals will be developed and the scope of the terms geometrical crystal filter and resonance piezoelectric crystal is intended to include all such new technologies a priori.

As used herein the term "about" refers to ±10%.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which, together with the above descriptions, illustrate the invention in a non limiting fashion.

Example 1

Determination of Wavelength for a Monochromatic Light

In its most simple configuration, apparatus 10 can serve as a wavelength meter for a monochromatic light, e.g., a laser light. When only a single wavelength is involved, the integration over the frequencies can be omitted and only one system parameter is preferably used. Thus, once the polarization phase-shift, $\Delta\Phi'$, is known (see Equation 8), the wavelength of the light can be extracted either by separated the light, e.g., using a beam splitter, into two detectors and calculating a contrast function, or, by employing the time-dependent polarization phase-shift, as further detailed hereinabove.

When extracting the wavelength using the contrast function, preferably wide bandwidth detectors are employed, up to GHZ, e.g., silicon or indium or gallium arsenide. In this embodiment, the response time of apparatus 10 is preferably in the GHz scale. Thus, apparatus 10 is capable of measuring transient phenomena unachievable with present technologies.

When a time-dependent polarization phase-shift is used, an additional tapping of the light is preferably employed before the crystal valve for the purpose of calibration. The overall relation between the initial frequency and the time-dependent polarization phase-shift is given by consideration of the following time-dependent amplitude:

$$U(f, V, \omega, t) = \cos^2 p_v \quad\quad (EQ. 21)$$
$$= \cos^2(p + aV\cos(\omega t))$$
$$= 0.5 + 0.5\cos(2p_0 + 2b(f - f_0) + 2aV\cos(\omega t)).$$

The frequency, hence the wavelength of the light is extracted using either Equation 21 or a calibration table. Alternately a Fourier transform with of the resulting signal can be obtained. The coefficients of the Fourier transform are Bessel function, $J_n$:

$$U(f, V, w, t) = DC + \quad\quad (EQ. 22)$$
$$0.5\left[\cos(2p_0 + 2b(f - f_0))J_0(2aV) + 2\cos(2p_0 + 2b(f - f_0))\right.$$
$$\sum_1^\infty (-1)^n J_{2n}(2aV)\cos(2n\omega t) - 2\sin(2p_0 +$$
$$\left.2b((f - f_0)) \times \sum_0^\infty (-1)^n J_{2n+1}(2aV)\cos\{(2n + 1)\omega t\}\right].$$

For a fixed voltage, V, one can extract, from the height of the first vs. the second peak, the value of $\tan(2p_0+2b(f-f_0))$, so that even a small variation in the frequency leads to a large change in the phase.

The typical free spectral range, 1/b, is from 100 GHZ to 10 GHZ. Experiments showed that much smaller variations of 200 MHZ can be observed.

In another embodiment, a least square fitting is used for fitting the terms in Equation 22 to multiple harmonics.

In an additional embodiment, a compensated pseudophase method is employed. According to a preferred embodiment of the present invention the pseudophase is extracted as the Arctangent of a linear combination of the even harmonics to a linear combination of the odd harmonics. One advantage of this definition is the possibility to adjust the dependence of the pseudophase on the Bessel parameter. For example, if the Bessel parameter is chosen to be, say, 3.05 (the maximum of the second harmonic $J_2$), a compensated pseudophase is constructed through a linear combination of $J_1$ and $J_3$. Specifically, a linear combination, $c_1 J_1 + c_3 J_3$, where $c_1$ and $c_3$ are constants, is constructed such that the variation of the pseudophase with the variation of the Bessel parameter is substantially small. One of ordinary skill in the art would appreciate that with this construction fluctuation of the current in crystal valve do not interfere with the Bessel parameter.

Example 2

Determination of Wavelength for Multichromatic Light

As stated, apparatus 10 can be used as a spectrometer, for the purpose of analyzing a signal having large frequency content. In this case, the output, after the crystal valve, can be written, in the wavelength representation, as:

$$U = \int \cos^2(\Delta\Phi(\lambda) + \Delta\Phi_{valve})I(\lambda)d\lambda, \quad\quad (EQ. 23)$$

where the $\cos^2$ dependence is due to the intensity modulation. Using trigonometric properties one arrives at the following expression:

$$2U = \int [\cos(2\Delta\Phi(\lambda) + 2\Delta\Phi_{valve}) + 1]I(\lambda)d\lambda \quad\quad (EQ. 24)$$
$$= \int [\cos(2\Delta\Phi(\lambda))\cos(2\Delta\Phi_{valve}) -$$
$$\sin(2\Delta\Phi(\lambda))\sin(2\Delta\Phi_{valve}) + 1]I(\lambda)d\lambda.$$

According to a preferred embodiment of the present invention $\Delta\Phi_{valve}$ as well as its dependence on time (e.g., periodic), is used so as extract the following individual terms from Equation 24.

$$U_{cos}(B) = 0.5 \int \cos((B(\lambda - \lambda_0))I(\lambda)d\lambda$$
$$U_{sin}(B) = 0.5 \int \sin((B(\lambda - \lambda_0))I(\lambda)d\lambda$$
$$U_{intg} = 0.5 \int I(\lambda)d\lambda. \quad\quad (EQ. 25)$$

In biological signals, the spectral dependence is typically modeled as a constant value plus a derivative. In this case, the constant term does not contribute to the time dependant signal and the time dependant signal is a direct measure of the derivative of the spectrum.

Generally, Equation 25 can be used by varying the system-parameter, B, so as to span a discrete basis and to extract $I(\lambda)$, e.g., using a Fourier transform or a least square fitting of $U_{cos}(B)$ and $U_{sin}(B)$. As stated, the variation of B can be done in more than one way, including, without limitation, varying (mechanically or electrically) the effective length of the geometrical crystal filter, rotating the geometrical crystal filter, further deflecting the light, providing a variable grating, and the like.

One of ordinary skill in the art would appreciate that $U_{cos}$ and $U_{sin}$ are Fourier transforms of the intensity. Thus, these quantities can be used directly to extract the time-dependent intensity for an incoherent source, even if the original source is coherent. This embodiment is useful in any case where it is desired to examine time-dependent properties.

Example 3

Wavelength Meter and Multi-wavelength Meter

Apparatus 10 can be used as a wavelength meter to measure, detect or qualify sharp spectral lines, distribution of light with a central wavelength, derivative of a distribution of light, doublet lines (either sharp or distributed), known multipeaks distributions for a small number of peaks and the like.

The natural dispersion of the grating creates a channel effect. In other words, unlike prior are systems, the angular dispersion of the grating is not used to measure the wavelength value, but rather as a much coarser effect to separate the wavelength into channels in order to measure at once several wavelengths with a small gap therebetween. Whether the wavelengths are sparse or ordered on a grid the multi-wavelength meter provides as much information as a spectrometer with the same wavelength span.

FIG. 7 shows a spectrum, decoded by a multi wavelength meter, in which each peak is covered by a separate detector or detectors. Since in this example each peak is separated over separate detectors, the extraction of the position of the peak is reduced to the problem of extracting a single peak in a wavelength meter.

Example 4

Spectrograph

As stated, apparatus 10 may serve as a spectrograph. The spectrograph can be based on the aforementioned multi-wavelength meter, a mathematical transform or a combination thereof.

In the spectrograph which is based on multi-wavelength meter, each pixel of a detector is defined as a separate wavelength meter channel and processed separately. On each channel, the quantity of information is substantially small, similar to a single line, a doublet or a derivative of the spectrum on a small interval. By a judicious design of the spectrograph, the information can appear on several contiguous channels, with different weights, for better evaluation of the parameters of the data.

In the spectrograph which is based on mathematical transform (Fourier or Gabor), the pseudophase is preferably recorded at a full range of values of the system-parameter, as further detailed hereinabove and a mathematical transform of the spectrum is recorded. Much information can be retrieved directly from the transform as is well known from signal processing theory. Although the mathematical procedure is more complex, the transform-based spectrograph has the huge advantage to be able to work with a single detector or a small number of detectors making it a good solution in the IR.

The spectrograph which is a combination between the transform-based spectrograph and the multi-wavelength meter spectrograph incorporates the advantages of both spectrographs, by making a transform on a small number of channels. It has also the advantage of compatibility with a two dimensional detector geometry, which fit better the existing detector technologies.

Any of the above spectrographs measures a spectrum in a range of wavelengths such that the output is a table of intensity values as function of wavelength. In addition, the spectrograph of the present embodiment is capable of measuring the derivative of a spectrum in a range of wavelengths, whereby the output is a table of derivative values as function of wavelength. This embodiment is particularly useful in continuous distribution when it is desired to quantify several constituents through their spectra. The processing of the data is referred to in the literature as quantitative spectroscopy methods and chemometrics.

More details on the mathematical procedure for evaluating the data can be found on: http://www.galactic.com/Algorithms/chem_preproc.htm.

The spectrograph of the present embodiment can also be used for measuring parameters which are related to the eigenvalues of the distribution based on a calibration model. In this embodiment, the output is a table of derivative values as function of wavelength. For such analysis, a combination of a transform-based spectrograph and a multi-wavelength meter spectrograph is preferably used. As the raw data is constituted of Fourier transform of the spectrum, adapted algorithms can be applied directly on the raw data, so as to directly calculate the scores of any type of principal component analysis method. This method substantially removes many of the errors related to the reconstruction and the algorithm and performs the analysis in a single step.

Example 5

General Applications

Following are potential uses of apparatus 10, according to a preferred embodiment of the present invention. As stated, apparatus 10 can serve as a wavelength meter, a multi-wavelength meter or a spectro graph. In applications in which a single wavelength is to be measured, a preferred configuration is the wavelength meter, whereas in applications inn which the light is formed of a plurality of wavelengths, either the multi-wavelength meter or the spectrograph can be employed, depending on the application.

Sharp Spectral Lines

As used herein, the term "sharp spectral line" refers to the case that the width of the light distribution along the central wavelength, full width half maximum, is less then ⅛ of the free spectral range of apparatus 10.

As used herein the term "free spectral range" refers to the range of wavelength which corresponds to a $2\pi$ change in the polarization phase.

In sharp spectral lines the peak wavelength and the center of gravity of the light distribution are considered as a single value, referred to as the peak wavelength. In this embodiment, apparatus 10 can be used to monitor the intensity and wavelength position for the many applications including, without limitations, laser wavelength measurement, emission of atomic or molecular lines and absorption spectral lines.

Distribution of Light with a Central Wavelength

When measuring the distribution of light with a central wavelength, the measured parameters by apparatus 10 are, preferably, the center of gravity of the wavelength distribution, the intensity of the light and, optionally and preferably a rough estimate of the width.

In many applications, the light distribution can be described as a distribution around a central value with a sizeable width. The transition from a sharp peak to a distribution is evaluated at ⅛ of the free spectral range. Above this value, when the distribution is below ⅓ of the free spectral range the situation can be regarded as in the case of sharp spectral line. In this case small loss of contrast occurs due to the width, and the fact that the apparatus 10 measures the center of gravity of the light, which is equivalent to the peak for symmetric distribution.

Additional rough information, through the contrast loss, is available on the width value. Above ⅓ of the free spectral range, apparatus 10 preferably measures with loss of performance up to the point that the information is lost with more and more uniform distribution, again, on the free spectral range scale.

According to a preferred embodiment of the present invention apparatus 10 is designed such that the width of the peak is below ⅓ of the free spectral ranges but cases may exist when such possibility is not feasible.

For a distribution of light, apparatus 10 can be used to monitor the intensity and wavelength position for the many applications, including, without limitations, Raman and vibrational spectroscopy, emission of atomic or molecular lines, absorption spectral lines and fiber Bragg gratings.

Derivative of a Distribution of Light

In this embodiment, the measured parameters are preferably the derivative of the light distribution and the total light.

The light distribution is preferably modeled as function of wavelength as a linear component with a constant value. This type of distribution is characteristic for many observed light distributions as for example fluorescent samples. In many cases, the information is carried by the (small) linear term.

Prior art systems record the total intensity as function of wavelength and retrieve the linear coefficient through differentiation. This process is known to result in erroneous results. According to a preferred embodiment of the present invention the derivative is physically separated from the bias on a separate signal and so can be retrieved directly.

Sharp or Distributed Doublet Lines

The measured parameters by apparatus 10 are, preferably, the peak or the center of gravity of the wavelength distribution of each one of the lines. Several different cases exist which depend on the additional knowledge available on the lines. The performances of the system depend strongly from the additional knowledge available.

If no additional information exists, apparatus 10 is capable of recognizing a doublet from a single line and to quantify the parameters when the distance between the lines is above ⅓ of the free spectral range and if the intensities of the lines are similar (similar derivation as Rayleigh criteria).

If the position of one line is known, as in the case for a laser exciter with a small satellite due to Raman or non-linear interaction, apparatus 10 is capable of measuring the second faint line substantially as if the first faint line was not present. This is preferably done by aligning apparatus 10 in a manner such that the first line has a pseudophase characterized in that all the energy is concentrated in the odd (or even) harmonics. Thus, any energy available in the even (odd) harmonics belongs to the second line.

Representative applications of in which apparatus 10 can be used, according to the presently preferred embodiment of the invention, include, without limitations, Raman or vibrational spectra, with the Raman line close to the exciter. The wavelength meter of the present invention is capable of detecting and measuring lines as close as a fraction of a nanometer.

Known Multipeaks Distributions for a Small Number of Peaks

In this application, the measured parameters by apparatus 10 describe a known multipeak distribution. If a certain spectral distribution is given, the apparatus 10 is preferably used to retrieve the coefficient of correlation of light distribution, under some constraints which are related to the information content of the distribution.

It will be appreciated that the concept of determining the presence of a complex spectra, in real-time, using a single wavelength meter, without the need of a complete spectrograph, has numerous potential applications.

Monitor Shifts due to External Conditions

Another example for potential application of apparatus 10 is monitoring shifts due to external conditions, such as, but not limited to, temperature changes, magnetic changes electric field changes or any other condition. The changes could be minute but still be measured, since, in a single measurement the center-of-gravity of the spectrum is measured, so that even if the spectrum is wide (say, hundreds of picometer, for example), its shift can be miniscule (less than a picometer) and still be measured.

Optical Computing

By its nature, apparatus 10 is appropriate for optical computing or signal processing. The reason is that when it is used in the configuration where there are two wedge regions and a variable time-delay, a Fourier-transform with variable time-dependent coefficient of the initial signal, is obtained.

Apparatus 10 can be used for optical computing and/or optical signal processing, especially when additional time and space dependencies are incorporated to the methods describe hereinabove, in order to improve the signal quality or measure simultaneously or sequentially separate or correlated spectral information.

Fiber Bragg Grating Sensor

A fiber Bragg grating sensor is a known device, in which one uses a broad-wavelength light and places along the fiber several Bragg sensors, which reflect at specific wavelengths. According to a preferred embodiment of the present invention apparatus 10 can be used as a fiber Bragg sensor.

The Bragg sensor may be formed in more than one way. In one embodiment, the Bragg sensor is preferably configured such that the light exits the optical fiber and enters apparatus 10. In apparatus 10 the light is analyzed simultaneously in several channels without any energy loss.

In another embodiment, the light source is preferably modulated using a chirp (frequency modulation) type modulation. In this case, several signals with a difference of time lag can be recorded on a single wavelength meter, or on a single pixel of a multi-wavelength meter, without any energy loss. Each signal appears, at a given time, as a different modulation frequency and the total signal contain several chirp with different parameters and can be separated by an appropriate algorithm.

Figures 8A, 8B:
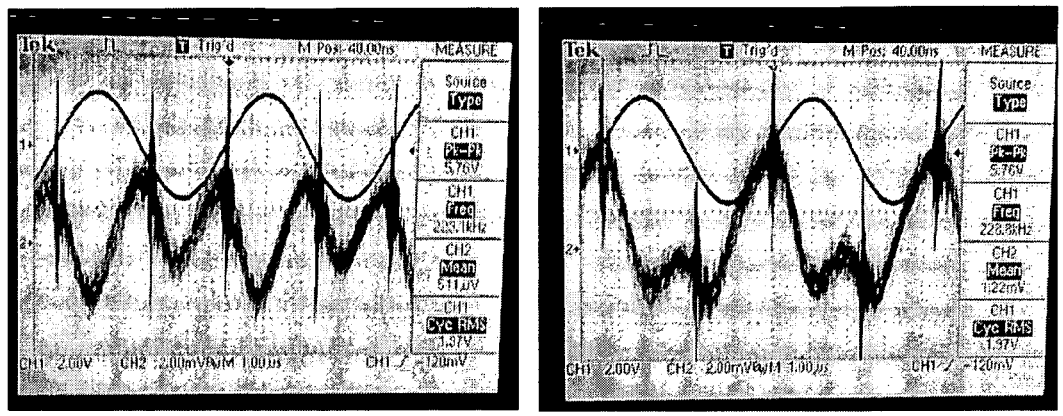
FIGS. 8a-b show a result of an experiment in which an equivalent 20 Km fiber was connected to a fiber Bragg sensor at the edge, according to a preferred embodiment of the present invention.

FIGS. 8*a-b* shows results of an experiment in which an equivalent 20 Km fiber was connected to a fiber Bragg sensor at the edge. Shown in FIGS. 8*a-b* is the result of applying a finger touch on the fiber. FIG. 8*a* shows the signal obtained from the fiber Bragg sensor without disturbance and FIG. 8*b* shows the signal for which a human finger touched the fiber Bragg sensor.

Example 6

Laser Wavelength Measurement

In this application, apparatus 10 records the intensity and the wavelength of a laser. The light of a laser is by essence monochromatic, and in most cases the wavelength distribution around the peak is negligible. The output of apparatus 10 is the intensity of light (in watts) as function of time and the wavelength of the light (in nm or related units) as function of time.

Many different lasers exist, covering a large spectrum of wavelength and with huge ratio of intensity and power. Typically, it is desired to measure the energy, for continuous lasers, or the power for pulsed lasers. In some applications, however, the laser wavelength modification influence the application of the laser and need to be monitored accurately.

Following are representative examples for potential applications of this embodiment of the invention, which are not to be considered as limiting.

Laser Monitoring and Control

According to a preferred embodiment of the present invention apparatus 10 is capable of measuring and characterizing dynamic effects, such as, but not limited to, mode hopping. For example, apparatus 10 can be used for finding or fixing the wavelength of a laser with unstable modes, so that the laser can hop from one mode to the next. According to a preferred embodiment of the present invention apparatus 10 automatically details the wavelength of the laser, and, if an active feedback loop is used, the frequency of the unstable laser is preferably fixed.

Tunable Laser Monitoring and Control

Tunable lasers are lasers in which the wavelength can be changed by an external process. Most prior art wavelength meters have a slow response (typically fractions of seconds). According to a preferred embodiment of the present invention apparatus 10 is capable of measuring, in real-time (milliseconds or microseconds), the wavelength of the tunable laser, with high accuracy. It will be appreciated that fast and accurate determination of the wavelength allows tunable laser to reach its target wavelength more efficiently.

DWDM Laser Monitoring

With the introduction of DWDM lasers in telecommunications, the position of the laser wavelength of different lasers, one relative to the other is of importance to avoid interference. Although this parameter is not of very much influence in present generation of DWDM lasers, which are typically separated by 200 or 100 GHz, it is recognized that the position of the laser wavelength is becoming more and more important, especially in future generations of 25 and 12.5 GHz when the natural fluctuations of the laser will begin to be sizeable.

According to a preferred embodiment of the present invention apparatus 10 is used for determining the position of the laser wavelength of different lasers in a telecommunication system.

Test of Wavelength Dependent Components

An important market is the test of wavelength dependant components in the telecommunication industry. Due to the stringent requirement of DWDM many critical components are tested individually or statistically. To date, the strategy being employed is a step-by-step strategy. In each step comprises controlling a tunable laser, which is driven to reach a given wavelength, stabilizing the laser at this wavelength and measuring, for example, the transmission or phase of the component at this wavelength.

According to a preferred embodiment of the present invention, apparatus 10 is used in real-time so that the measurement is made "on the fly." This can be done, for example, by measuring the wavelength using the natural sweep of the tunable laser, as further detailed hereinabove.

Another application is related to the capability of apparatus 10 to measure at low light level. This feature of the present embodiment can be exploited for measuring the wavelength at the detector side where the light intensity is significantly reduced.

Accurate Reference of the Wavelength for Laser Emitters

In some applications, as for example for Raman exciter, the exact wavelength of the laser is of importance because the result is a relative shift. Because of this the lasers which are used in these applications are either gas or solid-state lasers. Expensive laser diodes with a complex wavelength control are also employed. According to a preferred embodiment of the present invention apparatus 10 is used for monitoring, preferably in real-time, the wavelength of a laser diode. It will be appreciated that such accurate and fast measurement significantly reduces the need to use expensive diode lasers. Hence, the present embodiment successfully provides a method of correcting, in real-time, laser diode fluctuations, even for low cost laser diodes.

Wavelength Monitoring for Lithographic Applications

The specifications for lithography, for the new generations, have a very high level of accuracy and monitoring of the wavelength with high accuracy is required. Hence, according to a preferred embodiment of the present invention, apparatus 10 is used for measuring and monitoring the wavelength of a laser in a lithography apparatus.

Example 7

Atomic or Molecular Lines, Intensity and Position

According to a preferred embodiment f the present invention apparatus 10 can be used replace standard spectroscopic devices in many instruments. The combination of speed and accuracy, quantity of light and volume make it a major breakthrough in spectroscopic applications, including, without limitation, near-infrared, UV, visible, enhanced, polarization dependant spectroscopies.

In this type of applications the light distribution emitted, diffused or reflected from the observed object is quantified as (time dependant) intensity at a measured wavelength. The measurement values (and their uncertainties) available to the user are the intensity of light (in watts) as function of time and the wavelength of the light (in nm or related units) as function of time.

The paradigm of this type of applications is that a known physical process is observed in which a sharp peak is emitted by the observed object under an excitation either known or unknown. The emission can be created by a multitude of different physical processes, including, without limitation, atomic and molecular emission, plasma induced emission (LIBS or AES), electrical or magnetic interaction and incoherent optical interaction, such as Raman or fluorescence.

The information can be carried either by the presence of the light at a given wavelength (detection), the quantity of light or its time dependence, the behavior of the wavelength as function of time, either to characterize the object measured or to characterize the physical process which create the emission.

Atomic and Molecular Emission

Many applications need to record the atomic and molecular emission from an object to characterize its composition either to analyze its composition or to analyze contaminants. Many different effects create the emission, for example, electrical or magnetic interaction, X ray, chemical effects, coherent optical interaction, such as non linear interaction, electromagnetic interactions, such as photons, electrons, alpha or muons.

Potential applications for this embodiment of the invention include, without limitation, semiconductors, chemical analysis, geology and minerals, petroleum and gas industry, pharmaceutical industry and detection of contaminants in liquids, solids and gases.

The advantages of using apparatus 10 for these applications are the high light gathering capacity and the capability to operate in real time.

Incoherent Optical Interaction

Raman, vibrational spectrum and fluorescence deserve a separate topic due to the importance of these applications in the practical field. However, for Raman and vibrational spectra, and obviously for fluorescence, the condition of a sharp peak is seldom met and most of the cases belong to the distribution of light with a central wavelength case. The center of gravity of the line, which is the measured parameter, is the correct information, unlike prior art systems in which the complete or partial spectrum has to be determined by a calculation, hence adding complexity and noise to the result.

In Raman, the excitation laser is typically polarized. The effect of that source is strongly attenuated by using a polarizer in front of apparatus 10, so that only the Raman scattered light is passing through. The characteristic bandwidth is about 0.1-0.2 nm to be compared to the 1 nm of holographic notch filters. Apparatus 10 allow measurements of many Raman, or other excited wavelength, which were unattainable before.

Absorption Spectral Lines

Apparatus 10 is capable of measuring both a positive and a negative signal. In other words, an absorption line on a DC bias behaves in the same way as a emission line. This feature can be exploited in many applications which are related to absorption spectroscopy in which it is desired to directly measure the center of gravity of the line. For single lines a simple wavelength meter according to a preferred embodiment of the present invention allows to record and recognize the line and a multi-wavelength meter allows recording a simple spectrum without the need of a more complex instrument.

Example 8

Imaging

Any of the above variants of apparatus 10 can be used for imaging.

Figure 9:
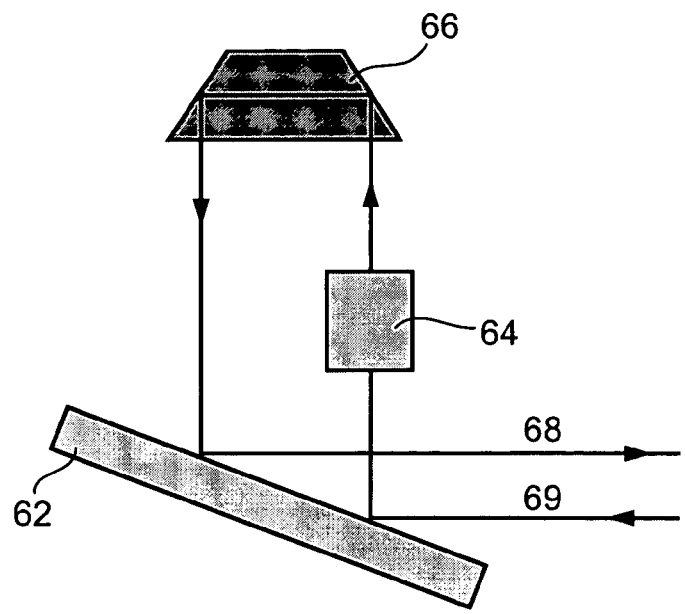
FIG. 9 is a simplified illustration of the apparatus of FIGS. 1a-c, in an embodiment in which the apparatus is used for imaging.

Reference is now made to FIG. 9, which is a simplified illustration of apparatus 10, in the embodiment in which apparatus 10 is used for imaging. According to a preferred embodiment of the present invention, when apparatus 10 is used for imaging, the light passes through the grating more than one time, so as to compensate for grating dispersion. For example, light ray 69 may enter grating 62, deflected thereby into geometrical crystal filter 64, and then redirected, e.g., using retro reflector 66, to re-enter grating 62. Alternatively, a second grating can be used. In any event, for each pixel of the image, apparatus 10 detects the emission of a particular frequency from the corresponding imager, thereby provides an extremely accurate and sharp image.

Table 1, below, lists the detector dimension for each one of the variants, in two models: compensated and uncompensated.

As used herein, the term compensated refers to an imaging in which the light is passing through a second grating in a manner that the image of a point source is also a point.

As used herein, the term uncompensated refers to an imaging in which a single grating is used, and the light is not passed through a second grating or prism to compensate for the dispersion.

The dimensionality of the data represents the number of dimensions of the detector. For example, if the detector is a single detector (or a dual detector separated by a polarization splitter) and if the optical scheme is compensated a full two dimensional imaging can be performed on the source in order to create a full spectral imager. This set-up is referred in the literature as achromatic grating set-up. The advantage of the use of apparatus 10 for achromatic grating is that in apparatus 10, unlike prior art systems, the information is carried in the time domain and can be measured separately for each point of an image.

TABLE 1

| Instrument | Detector dimension | Imaging capacity |
|---|---|---|
| WM | 0, point detector | 1D and 2D |
| MWM | 1D | 1D |
| SMWM | 1D | 1D |

TABLE 1-continued

| Instrument | Detector dimension | Imaging capacity |
|---|---|---|
| Transform spectrograph- sequential | 0, point detector | 1D and 2D |
| Transform spectrograph- parallel | 1D | 1D |
| Time frequency spectrograph - sequential | 1D | 1D |
| Time frequency spectrograph - parallel | 2D | No |

If the detector is a one dimensional array as for example the multi-wavelength meter, the imaging is preferably done in the perpendicular direction in order to create a one-dimensional parallel measurement using anamorphic optics, and to acquire at once a complete line of an object in one shot. The imaging multi-wavelength meter can be used in a two-dimensional detector when each line (or column) of the detector behaves as a separate multi-wavelength meter.

The frequency of the crystals is preferably adapted to the lower frequency of the two dimensional detectors. This can be done, for example, by modulating the source at a frequency close to the crystal and its harmonics in order to create a beat frequency, as further detailed hereinabove. This embodiment has the advantages of modulation on modulation, in which only light modulated both by the laser and by the crystal contributes to the signal, thus removing many artifacts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for analyzing light having at least one wavelength, the apparatus comprising:

(a) a light deflector for deflecting the light so as to provide a deflected light beam characterized by at least one wavelength-dependent angle, respectively, corresponding to the at least one wavelength of the light;

(b) an encoder, which comprises at least one birefringent crystal and which is capable of generating at least one angle-dependent polarization phase-shift in said deflected light beam so as to provide an encoded light beam characterized by at least one angle-dependent polarization phase-shift, respectively corresponding to said at least one wavelength-dependent angle; and (c) a decoder, for decoding said encoded light beam so as to determine, for each angle-dependent polarization phase-shift, a wavelength corresponding to said angle-dependent polarization phase-shift.

2. The apparatus of claim 1, serving as a component in a system or device selected from the group consisting of a wavelength amplifying system, an optical sensor, a spectrograph, an imaging spectrograph, a time-frequency spectrograph, a telecentric imaging system, an optical storage medium, an optical communication system, a tunable laser system, a lithography system, an optical computing system and a fiber Bragg sensor.

3. The apparatus of claim 1, serving for performing at least one operation selected from the group consisting of stabilizing laser radiation, monitoring optical pulses, modulating a light source, discriminating between Raman emission and fluorescence, discriminating between different light sources, testing a multi-lasers test system, generating frequency multiplexed signals and sensing changes in environmental conditions, influencing said deflected light beam and/or said encoded light beam.

4. The apparatus of claim 3, wherein said changes in said environmental conditions are selected from the group consisting of vibrations, changes in temperature, changes in pressure, changes in magnetic field and changes in electric field.

5. The apparatus of claim 1, further comprising:
(d) a mechanism for varying at least one parameter representing at least one of said light deflector and said encoder so as to span a discrete basis of signals, each corresponding to one value of said at least one parameter.

6. The apparatus of claim 5, wherein said decoder is operable to use said discrete basis of signals for determining wavelengths.

7. The apparatus of claim 1, further comprising a beam splitter positioned on a light-path of the light before impingement of the light on said light deflector, for splitting the light into two beams, each having a predetermined polarization.

8. The apparatus of claim 7, further comprising at least one polarization rotator, designed and configured so as to rotate a polarization of said deflected light beam and/or a polarization of said encoded light beam.

9. The apparatus of claim 1, wherein said light deflector is selected from the group consisting of a grating and a prism.

10. The apparatus of claim 9, wherein said grating is characterized by a first grating equation in a first dimension and a second grating equation in a second dimension.

11. The apparatus of claim 1, wherein said encoder is calibrated so as to generate a zero or small polarization phase-shift for a predetermined set of wavelengths and a non-zero polarization phase-shift for wavelengths other than said predetermined set of wavelengths.

12. The apparatus of claim 1, further comprising a first mechanism for varying said angle-dependent polarization phase-shift.

13. The apparatus of claim 12, wherein said first mechanism is operable to rotate said at least one birefringent crystal about an axis, so as to vary said angle-dependent polarization phase-shift.

14. The apparatus of claim 13, further comprising a first polarization rotator, for rotating a polarization of said deflected light beam from a first polarization orientation to a second polarization orientation.

15. The apparatus of claim 14, wherein said first polarization rotator is designed and constructed such that said second polarization orientation substantially equals an orientation of said at least one birefringent crystal.

16. The apparatus of claim 15, further comprising a second polarization rotator, for rotating a polarization of said encoded light beam from said second polarization orientation to said first polarization orientation.

17. The apparatus of claim 12, wherein said first mechanism is operable to generate a further deflection of the deflected light beam, said further deflection being time-dependent so that said angle-dependent polarization phase-shift varies.

18. The apparatus of claim 12, wherein said first mechanism is operable to vary an effective length of said at least one birefringent crystal, thereby to vary said angle-dependent polarization phase-shift.

19. The apparatus of claim 18, wherein said first mechanism is capable of applying a voltage on said at least one birefringent crystal, thereby to vary said effective length.

20. The apparatus of claim 18, wherein a shape of said at least one birefringent crystal is selected such that when said first mechanism applies a translational motion thereto, said effective length is varied.

21. The apparatus of claim 12, wherein said light deflector is a dynamic grating characterized by a grating equation and further wherein said first mechanism is operable to vary said grating equation, thereby to vary said wavelength-dependent angle, thereby also to vary said angle-dependent polarization phase-shift.

22. The apparatus of claim 1, further comprising at least one geometrical crystal filter, for polarizing the light prior to impinging of the light on said light deflector.

23. The apparatus of claim 1, wherein said decoder is capable of splitting said encoded light beam into two secondary polarized light beams, and calculating a contrast function between said two secondary polarized light beams.

24. The apparatus of claim 1, wherein said decoder is capable of generating a representative time-delay for each polarization state, and using said representative time-delay for determining said at least one spectral component of the light.

25. The apparatus of claim 24, wherein said decoder comprises:
(i) a temporal polarization phase-shifter, communicating with an external clock, and capable of accumulating a time-dependent polarization phase-shift to said encoded light beam; and
(ii) a polarization phase-shift analyzer, capable of analyzing said time-dependent polarization phase-shift so as to provide an optical signal having a time-dependent intensity, corresponding to said time-dependent polarization phase-shift.

26. The apparatus of claim 25, wherein said decoder further comprises an optical converter, for converting said optical signal to electrical signal.

27. The apparatus of claim 1, further comprising at least one filter for filtering a portion of the light, prior to an impingement on said deflector, said encoder and/or said decoder.

28. The apparatus of claim 1, further comprising a first anamorphic prism, positioned so as to reduce a spot size of the light prior to impingement of the light on said deflector.

29. The apparatus of claim 1, further comprising an anamorphic prism, positioned so as to increase angular dispersion of said deflected light beam, prior to impingement of said deflected light beam on said decoder, thereby to optimize a wavelength resolution.

30. The apparatus of claim 1, further comprising a low-resolution optical device, for determining a low-resolution spectral range of the light, said low-resolution optical device being characterized by a spectral resolution which is lower than a spectral resolution of said decoder.

31. The apparatus of claim 30, wherein said low-resolution optical device comprises an additional geometrical crystal filter, and further wherein a free spectral range of said additional geometrical crystal filter is different than a free spectral range of said at least one birefringent crystal.

32. The apparatus of claim 31, wherein said free spectral range of said additional geometrical crystal filter is substantially larger than said free spectral range of said at least one birefringent crystal.

33. The apparatus of claim 30, wherein said low-resolution optical device is capable of directly using said at least one wavelength-dependent angle so as to determine said low-resolution spectral range.

34. The apparatus of claim 33, wherein said low-resolution optical device is a position sensing device, whereby a position of said deflected light beam corresponds to a respective wavelength-dependent angle.

35. The apparatus of claim 1, wherein the apparatus is characterized by a sub picometer resolution.

36. The apparatus of claim 1, wherein the apparatus is characterized by a sub nanometer resolution.

37. The apparatus of claim 1, wherein the apparatus is characterized by a total analysis time of from about 1 nanosecond to a few hours.

38. The apparatus of claim 1, wherein the apparatus is characterized by a detectivity of from about −80 db to about −0 db.

39. An apparatus for measuring a wavelength of a monochromatic light, the apparatus comprising:
(a) a light deflector for deflecting the monochromatic light at a wavelength-dependent angle;
(b) an encoder, capable generating in the monochromatic light at least one angle-dependent polarization phase-shift corresponding to said wavelength-dependent angle thereby to provide an encoded light beam; and
(c) a decoder, for decoding said encoded light beam so as to determine a wavelength corresponding to said angle-dependent polarization phase-shift.

40. The apparatus of claim 39, serving as a component in device or a system selected from the group consisting of a wavelength amplifying system, an optical sensor, an optical storage medium, a tunable laser system, and an optical computing system.

41. A communications system having a multiplexing apparatus for generating an optical signal characterized by a plurality of wavelengths and a de-multiplexing apparatus, for extracting said information from the optical signal, the de-multiplexing apparatus comprising:
(a) a light deflector for deflecting the light so as to provide a deflected light beam characterized by a plurality of wavelength-dependent angles, respectively, corresponding to the plurality of wavelengths of the optical signal;
(b) an encoder, capable of generating at least one angle-dependent polarization phase-shift in said deflected light beam so as to provide an encoded light beam characterized by a plurality of angle-dependent polarization phase-shift, respectively corresponding to said plurality of wavelength-dependent angles; and
(c) a decoder, for determining the plurality of wavelengths of the optical signal based on said plurality of polarization phase-shifts.

42. A Bragg sensor system for detecting vibrations, the Bragg sensor system comprising the apparatus of claim 1.

43. A method of analyzing light having at least one wavelength, the method comprising:
(a) deflecting the light so as to provide a deflected light beam characterized by at least one wavelength-dependent angle, respectively, corresponding to the at least one wavelength of the light;
(b) encoding said deflected light beam using at least one birefringent crystal so as to generate at least one angle-dependent polarization phase-shift in said deflected light beam, thereby providing an encoded light beam characterized by at least one angle-dependent polarization phase-shift, respectively corresponding to said at least one wavelength-dependent angle; and
(c) decoding said encoded light beam so as to determine, for each angle-dependent polarization phase-shift, a wavelength corresponding to said angle-dependent polarization phase-shift;
thereby analyzing the light.

44. A method of measuring a wavelength of a monochromatic light, the method comprising:
(a) deflecting the monochromatic light at a wavelength-dependent angle;
(b) encoding the monochromatic light using at least one birefringent crystal so as to generate in the monochromatic light at least one angle-dependent polarization phase-shift corresponding to said wavelength-dependent angle, thereby providing an encoded light beam; and
(c) decoding said encoded light beam so as to determine a wavelength corresponding to said angle-dependent polarization phase-shift;
thereby measuring the wavelength of the monochromatic light.

45. A method of sensing changes in environmental conditions affecting a wavelength of light, the method comprising executing the method of claim 43 for determining wavelength changes in the light, thereby sensing the changes in environmental conditions.

46. Apparatus for analyzing light having at least one wavelength, the apparatus comprising:
(a) a grating characterized by a first grating equation in a first dimension and a second grating equation in a second dimension, for deflecting the light so as to provide a deflected light beam characterized by at least one wavelength-dependent angle, respectively, corresponding to the at least one wavelength of the light;
(b) an encoder, capable of encoding said deflected light beam so as to provide an encoded light beam characterized by at least one angle-dependent polarization state, respectively, corresponding to said at least one wavelength-dependent angle; and
(c) a decoder, for decoding said encoded light beam so as to determine at least one spectral component of the light.

* * * * *